US012595298B2

(12) United States Patent
Yuan et al.

(10) Patent No.: US 12,595,298 B2
(45) Date of Patent: Apr. 7, 2026

(54) ANTI-NGF ANTIBODY AND ANTIGEN-BINDING FRAGMENT THEREOF, PREPARATION METHOD, AND APPLICATION THEREOF

(71) Applicant: XIYUAN ANJIAN MEDICINE (SHANGHAI) CO., LTD, Shanghai (CN)

(72) Inventors: Xiaohui Yuan, Hangzhou (CN); Guoyong Wang, Hangzhou (CN); Yujiao Liu, Hangzhou (CN); Donghong Zheng, Hangzhou (CN)

(73) Assignee: XIYUAN ANJIAN MEDICINE (SHANGHAI) CO., LTD, Shanghai (CN)

( * ) Notice: Subject to any disclaimer, the term of this patent is extended or adjusted under 35 U.S.C. 154(b) by 772 days.

(21) Appl. No.: 17/906,190

(22) PCT Filed: Aug. 2, 2021

(86) PCT No.: PCT/CN2021/109995
§ 371 (c)(1),
(2) Date: Sep. 12, 2022

(87) PCT Pub. No.: WO2022/028354
PCT Pub. Date: Feb. 10, 2022

(65) Prior Publication Data
US 2023/0109780 A1 Apr. 13, 2023

(30) Foreign Application Priority Data
Aug. 6, 2020 (CN) .......................... 202010780690.2

(51) Int. Cl.
*C07K 16/22* (2006.01)
*A61P 29/00* (2006.01)
*A61K 39/00* (2006.01)

(52) U.S. Cl.
CPC .............. *C07K 16/22* (2013.01); *A61P 29/00* (2018.01); *A61K 2039/505* (2013.01); *C07K 2317/24* (2013.01); *C07K 2317/76* (2013.01); *C07K 2317/92* (2013.01)

(58) Field of Classification Search
CPC ........ C07K 16/22; C07K 16/46; C12N 15/13; C12N 15/63; C12N 5/00; A61K 39/395
USPC ...................................... 424/158.1
See application file for complete search history.

(56) References Cited

FOREIGN PATENT DOCUMENTS

| CN | 104910274 | A | | 9/2015 | |
|---|---|---|---|---|---|
| CN | 108178798 | | * | 6/2018 | ............. C07K 16/22 424/143.1 |
| CN | 108178798 | A | | 6/2018 | |
| CN | 108473553 | A | | 8/2018 | |
| CN | 112625128 | A | | 4/2021 | |
| JP | 2010535509 | A | | 11/2010 | |
| WO | 2005061540 | A2 | | 7/2005 | |
| WO | 2010128398 | A1 | | 11/2010 | |
| WO | 2016077666 | A1 | | 5/2016 | |

OTHER PUBLICATIONS

Ma (Modern Drug Discovery 2004, 7(6)). (Year: 2004).*
Steinman et al (Nat Med. Jan. 6, 2012;18(1):59-65). (Year: 2012).*
Blumberg et al (Nat Med.; 18(1): 35-41. (Year: 2015).*
Cohen (Cells. Mar. 14, 2024;13(6):511). (Year: 2024).*
Pangalos et al (Nature Reviews Drug Discovery 6, 521-532 (Jul. 2007)) . . . (Year: 2007).*
Van Velzen et al (Front Pain Res (Lausanne). Aug. 7, 2020;1. (Year: 2020).*
DeWitt et al, J Neurotrauma. Dec. 1, 2018;35(23):2737-2754). (Year: 2018).*
International Search Report issued in International Application No. PCT/CN2021/109995; mailed Nov. 9, 2021; 15 pgs.
Written Opinion of the International Search Authority issued in International Application No. PCT/CN2021/109995; mailed Nov. 9, 2021; 10 pgs.
Search Report issued in Chinese Application No. 202010780690.2; mailed Mar. 4, 2022; 2 pgs.
First Office Action issued in Chinese Application No. 202010780690. 2; mailed Mar. 9, 2022; 12 pgs.

* cited by examiner

*Primary Examiner* — Vanessa L. Ford
(74) *Attorney, Agent, or Firm* — HAUPTMAN HAM, LLP

(57) ABSTRACT

Provided are an anti-NGF antibody or an antigen-binding fragment thereof, a preparation method and an application thereof. Also provided is an isolated polynucleotide encoding the anti-NGF antibody or the antigen-binding fragment thereof, as well as a vector containing the isolated polynucleotide. Also provided is use of the antibody or the antigen-binding fragment thereof of the present invention in preparing the medicament for the treatment of NGF-mediated diseases or disorders.

6 Claims, 16 Drawing Sheets

Specification includes a Sequence Listing.

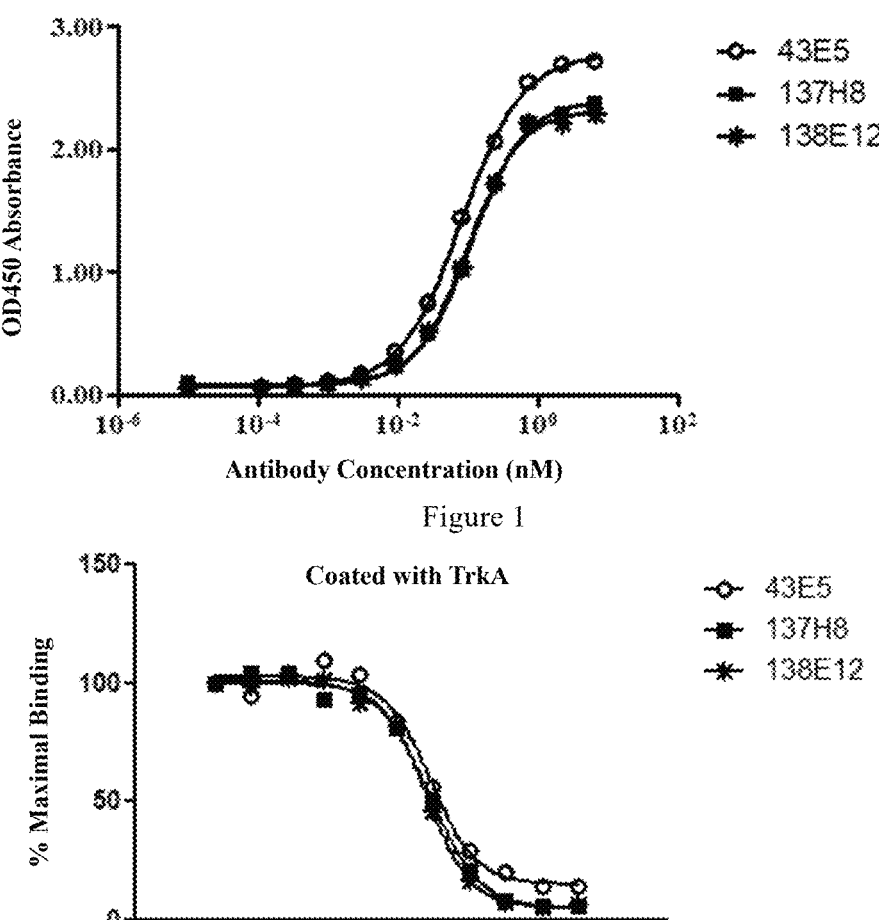
Figure 1
Figure 2A
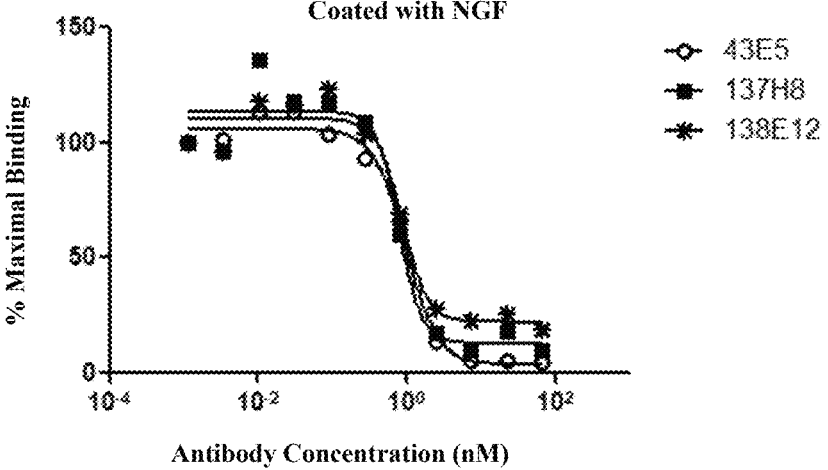
Figure 2B

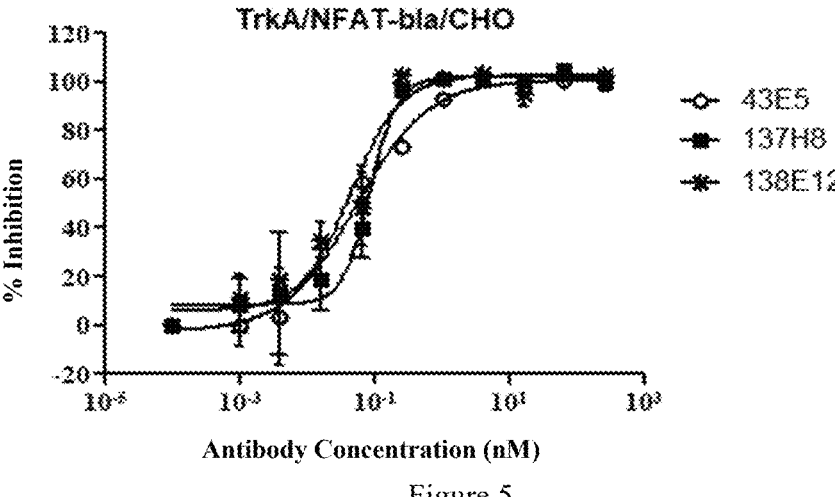
Figure 5
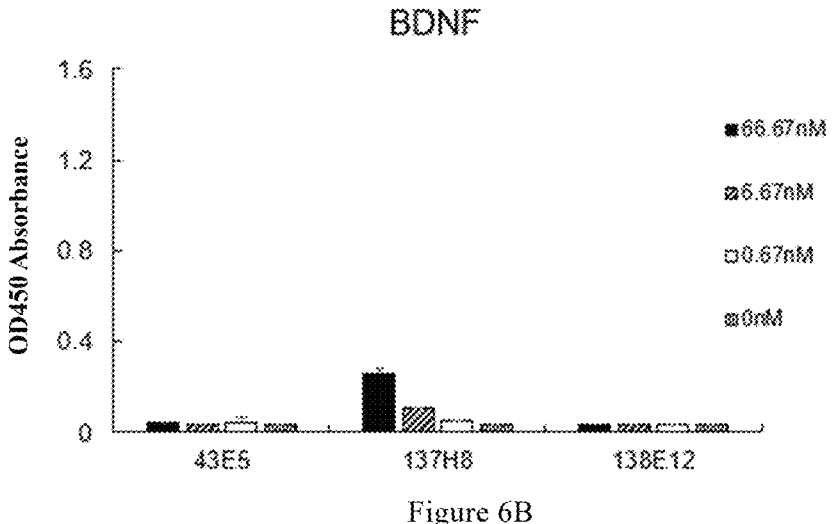
Figure 6A
Figure 6B

Ligand: NGF-Biotin
Binding 1: 138E12
Binding 2: 138E12

Ligand: NGF-Biotin
Binding 1: 138E12
Binding 2: 43E5

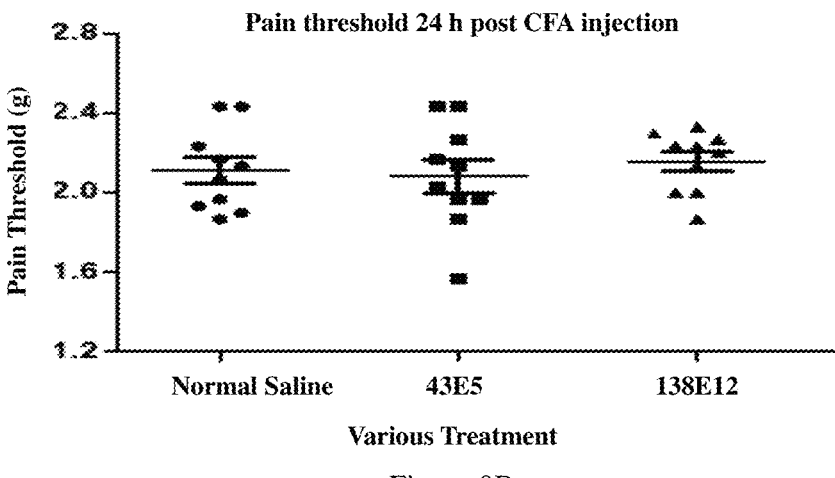
Figure 8B
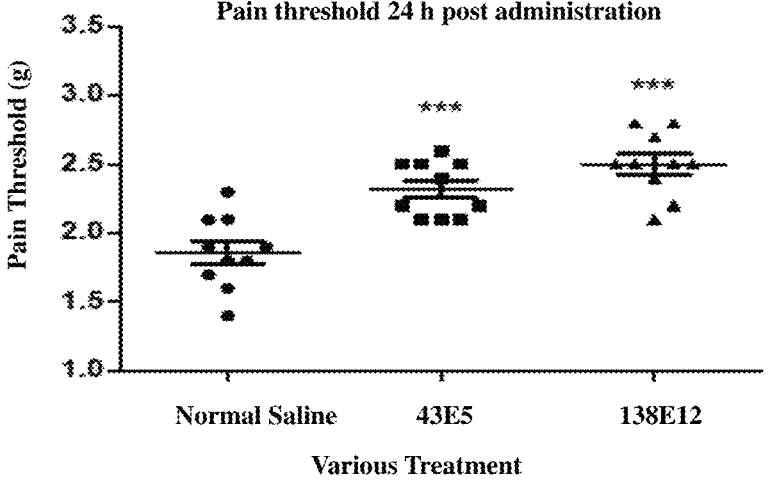
Figure 8C
Figure 8D

ANTI-NGF ANTIBODY AND ANTIGEN-BINDING FRAGMENT THEREOF, PREPARATION METHOD, AND APPLICATION THEREOF

RELATED APPLICATIONS

The present application is a U.S. National Phase of International Application No. PCT/CN2021/109995, filed Aug. 2, 2021, and claims priority to Chinese Application No. 202010780690.2, filed Aug. 6, 2020.

INCORPORATION BY REFERENCE

The sequence listing provided in the file entitled SEQUENCE_LISTING_V2.txt, which is an ASCII text file that was created on Jul. 22, 2022, and which comprises 43,025 bytes, is hereby incorporated by reference in its entirety.

FIELD OF THE INVENTION

The present invention belongs to the technical field of biological immunity. In particular, it relates to an anti-NGF antibody capable of specifically binding to human nerve growth factor and antigen-binding fragment thereof, and also relates to a preparation method and use of the antibody and antigen-binding fragment thereof.

BACKGROUND OF THE INVENTION

Nerve Growth Factor (NGF) is the first identified neurotrophic factor, and its role in the development and survival of peripheral and central neuronal has been characterized. NGF has been shown to be a key survival and maintenance factor in the development of peripheral sympathetic and embryonic sensory neurons and basal forebrain cholinergic neurons (Smeyne et al. (1994) Nature, 368:246-249; Crowley et al. (1994) Cell, 76:1001-1011), which upregulates the expression of neuropeptide in sensory neurons (Lindsay et al. (1989) Nature, 337:362-364). NGF comprises three subunits, α, β and γ, among which β is the active subunit of NGF. Currently, NGF is known to modulate its activity by two distinct membrane surface receptors: TrkA tyrosine kinase receptor (Trpomyosin receptor kinase A, TrkA, also known as the "high-affinity" NGF receptor) and p75 common neurotrophin receptor (p75 neurotrophin receptor, p75NTR, also known as the "low-affinity" NGF receptor) (Chao et al. (1986) Science, 232:518-521).

NGF/TrkA signaling pathway is closely related to pain and can mediate the occurrence of pain. In the injured and inflammatory tissues, NGF is highly expressed, and the activation of nociceptive neurons by TrkA is triggered by multiple mechanisms, resulting in pain signals. After injected with NGF, thermal stimulus-induced paw withdrawal latency in rats was significantly shortened (Lewin et al. (1994) Eur J Neurosci, 6:1903-1912). In animal models, inflammation-related pain can be significantly reduced by administering NGF antibodies, TrkA-IgG and the like to neutralize NGF activity (Woolf C J et al. (1994) Neuroscience, 62:327-331; McMahon S B et al. (1995) Net. Med. 1:774-780; Koltzenburg M et al. (1999) Eur. J. Neurosci. 11:1698-1704), suggesting that increased levels of NGF are required for the development of systemic hyperalgesia. The NGF content was significantly increased in synovial fluid of patients with rheumatoid arthritis, whereas NGF was not detected in the synovial fluid of non-inflammatory patients (Aloe et al. (1992) Arthritis and Rheumatism, 35:351-355). After injected with NGF, healthy person would suffer from hyperalgesia and localized pain (Petty et al. (1994) Ann Neurol, 36:244-246). Homozygous missense mutations in the NGF β gene can cause HSANS symptoms in humans, such patients are insensitive to pain, cold, and heat (Larsson et al. (2009) Neurobiol Dis, 33:221-228). The NTRK1 gene encodes the TrkA protein, and its polymorphisms are closely associated with changes in pain perception. Autosomal recessive mutations in exon 17 of NTRK1 will cause congenital hypoalgesia with anhidrosis (Indo et al. (1996) Nature genetics, 13:485-488).

Globally, tens of millions of patients are suffering from chronic pain, and this number continues to increase as the population increases. Currently, agents clinically used for the treatment of chronic pain include non-steroidal anti-inflammatory agents, anticonvulsants, opioids, etc. However, these agents have many disadvantages. Among them, the non-steroidal anti-inflammatory agents have limited efficacy, and have side effects including gastrointestinal bleeding and kidney toxicity; while opioids have side effects such as addiction. There is an urgent need for pain-relieving, non-toxic, and abuse-resistant non-opioid analgesics in this field, and the value of a method for the treatment of chronic pain by inhibiting NGF is thus very clear. To date, there are many anti-human NGF antibodies in R&D or clinical development stage, among which the most advanced ones include Pfizer/Lilly's anti-NGF monoclonal antibody Tanezumab and Regeneron/Sanofi's Fasinumab. Tanezumab, the first developed anti-NGF antibody agent, has been reported to exhibit potent and wide-ranging analgesic effects on joint pain associated with degenerative joint disease, chronic low back pain, bladder pain associated with interstitial cystitis and the like (Lane N E et al. (2010) N Engl J Med, 363:1521-1531). The agent is currently undergoing phase III clinical trials for indications such as osteoarthritis, back pain, and cancer pain. Data from a Phase II/III clinical study of Fasinumab in the treatment of osteoarthritic pain have shown that patients treated with 4 doses of Fasinumab achieved statistically significant improvements in pain relief. On the other hand, clinical trials of multiple NGF inhibitors have also shown that NGF antibodies may face problems such as being restricted to severely ill people, not for a long-term use, and dose limitations, making the clinical application of NGF antibodies need further safety verification.

NGF is an extremely important factor for neuronal development, therefore, the effect of NGF dose on neurons should also be considered when developing agents that inhibit NGF function. In one aspect, the effective dose of an antibody agent depends on the neutralizing activity on the antigen and the amount of the antigen present in the body, and an increase in the neutralizing activity is correlated with a decrease in the dose administered. We need to obtain CDR regions against different antigen epitopes or against the same epitope with different affinities in anti-NGF antibody research. Different CDRs have different immunogenicity, resulting in different antibody tolerance rates and toxicity, which directly affect the efficacy. In another aspect, the immune response caused by the antibody in the subject will result in forming immune complexes, altering the pharmacokinetics, producing allergic reactions, etc., thereby eliminating the therapeutic use. The human immune system has minimal antibody response to humanized antibodies compared to murine and chimeric antibodies, meanwhile, the humanized antibodies have half-life similar to that of natural human antibodies, which ensures less dosing frequency and lower dosage.

Therefore, it is extremely important to develop anti-NGF antibodies with higher affinity and specificity, and to humanize the antibodies for the treatment or prevention of various diseases associated with NGF.

SUMMARY OF THE INVENTION

Based on the deficiency of the prior art, the main purpose of the present invention is to provide an anti-NGF antibody with high affinity, strong specificity and significant efficiency. The present invention also provides the preparation method and use of the antibody.

In one aspect, the present invention provides an anti-NGF antibody or antigen-binding fragment thereof capable of specifically binding to NGF, the antibody or antigen-binding fragment thereof comprising:

(a) a heavy chain variable region (VH) comprising the following three complementarity determining regions (CDRs):

(i) VH CDR1 consisting of the following sequence: SEQ ID NO: 13, or a sequence having a substitution, deletion or addition of one or more amino acids (e.g. a substitution, deletion or addition of 1, 2 or 3 amino acids) compared thereto, (ii) VH CDR2 consisting of the following sequence: SEQ ID NO: 14, or a sequence having a substitution, deletion or addition of one or more amino acids (e.g. a substitution, deletion or addition of 1, 2 or 3 amino acids) compared thereto, and (iii) VH CDR3 consisting of the following sequence: SEQ ID NO: 15, or a sequence having a substitution, deletion or addition of one or more amino acids (e.g. a substitution, deletion or addition of 1, 2 or 3 amino acids) compared thereto, and/or (b) a light chain variable region (VL) comprising the following three complementarity determining regions (CDRs):

(iv) VL CDR1 consisting of the following sequence: SEQ ID NO: 22, or a sequence having a substitution, deletion or addition of one or more amino acids (e.g. a substitution, deletion or addition of 1, 2 or 3 amino acids) compared thereto, (v) VL CDR2 consisting of the following sequence: SEQ ID NO: 23, or a sequence having a substitution, deletion or addition of one or more amino acids (e.g. a substitution, deletion or addition of 1, 2 or 3 amino acids) compared thereto, and (vi) VL CDR3 consisting of the following sequence: SEQ ID NO: 24, or a sequence having a substitution, deletion or addition of one or more amino acids (e.g. a substitution, deletion or addition of 1, 2 or 3 amino acids) compared thereto, preferably, the substitution described in any one of (i)-(vi) is a conservative substitution;

preferably, the VH of the antibody or antigen-binding fragment thereof comprises: VH CDR1 as shown in SEQ ID NO: 13, VH CDR2 as shown in SEQ ID NO: 14 and VH CDR3 as shown in SEQ ID NO: 15, and the VL of the antibody or antigen-binding fragment thereof comprises: VL CDR1 as shown in SEQ ID NO: 22, VL CDR2 as shown in SEQ ID NO: 23, and VL CDR3 as shown in SEQ ID NO: 24.

In one aspect, the present invention provides an anti-NGF antibody or antigen-binding fragment thereof capable of specifically binding to NGF, the antibody or antigen-binding fragment thereof comprising:

(a) a heavy chain variable region (VH) comprising the following three complementarity determining regions (CDRs):

(i) VH CDR1 consisting of the following sequence: SEQ ID NO: 16, or a sequence having a substitution, deletion or addition of one or more amino acids (e.g. a substitution, deletion or addition of 1, 2 or 3 amino acids) compared thereto, (ii) VH CDR2 consisting of the following sequence: SEQ ID NO: 17, or a sequence having a substitution, deletion or addition of one or more amino acids (e.g. a substitution, deletion or addition of 1, 2 or 3 amino acids) compared thereto, and (iii) VH CDR3 consisting of the following sequence: SEQ ID NO: 18, or a sequence having a substitution, deletion or addition of one or more amino acids (e.g. a substitution, deletion or addition of 1, 2 or 3 amino acids) compared thereto, and/or (b) a light chain variable region (VL) comprising the following three complementarity determining regions (CDRs):

(iv) VL CDR1 consisting of the following sequence: SEQ ID NO: 25, or a sequence having a substitution, deletion or addition of one or more amino acids (e.g. a substitution, deletion or addition of 1, 2 or 3 amino acids) compared thereto, (v) VL CDR2 consisting of the following sequence: SEQ ID NO: 26, or a sequence having a substitution, deletion or addition of one or more amino acids (e.g. a substitution, deletion or addition of 1, 2 or 3 amino acids) compared thereto, and (vi) VL CDR3 consisting of the following sequence: SEQ ID NO: 27, or a sequence having a substitution, deletion or addition of one or more amino acids (e.g. a substitution, deletion or addition of 1, 2 or 3 amino acids) compared thereto, preferably, the substitution described in any one of (i)-(vi) is a conservative substitution;

preferably, the VH of the antibody or antigen-binding fragment thereof comprises: VH CDR1 as shown in SEQ ID NO: 16, VH CDR2 as shown in SEQ ID NO: 17 and VH CDR3 as shown in SEQ ID NO: 18, and the VL of the antibody or antigen-binding fragment thereof comprises: VL CDR1 as shown in SEQ ID NO: 25, VL CDR2 as shown in SEQ ID NO: 26, and VL CDR3 as shown in SEQ ID NO: 27.

In one aspect, the present invention provides an anti-NGF antibody or antigen-binding fragment thereof capable of specifically binding to NGF, the antibody or antigen-binding fragment thereof comprising:

(a) a heavy chain variable region (VH) comprising the following three complementarity determining regions (CDRs):

(i) VH CDR1 consisting of the following sequence: SEQ ID NO: 19, or a sequence having a substitution, deletion or addition of one or more amino acids (e.g. a substitution, deletion or addition of 1, 2 or 3 amino acids) compared thereto, (ii) VH CDR2 consisting of the following sequence: SEQ ID NO: 20, or a sequence having a substitution, deletion or addition of one or more amino acids (e.g. a substitution, deletion or addition of 1, 2 or 3 amino acids) compared thereto, and (iii) VH CDR3 consisting of the following sequence: SEQ ID NO: 21, or a sequence having a substitution, deletion or addition of one or more amino acids (e.g. a substitution, deletion or addition of 1, 2 or 3 amino acids) compared thereto, and/or (b) a light chain variable region (VL) comprising the following three complementarity determining regions (CDRs):

(iv) VL CDR1 consisting of the following sequence: SEQ ID NO: 28, or a sequence having a substitution, deletion or addition of one or more amino acids (e.g. a substitution, deletion or addition of 1, 2 or 3 amino acids) compared thereto, (v) VL CDR2 consisting of the following sequence: SEQ ID NO: 29, or a sequence having a substitution, deletion or addition of one or more amino acids (e.g. a substitution, deletion or addition of 1, 2 or 3 amino acids) compared thereto, and (vi) VL CDR3 consisting of the following sequence: SEQ ID NO: 30, or a sequence having a substitution, deletion or addition of one or more amino acids (e.g. a substitution, deletion or addition of 1, 2 or 3 amino acids) compared thereto, preferably, the substitution described in any one of (i)-(vi) is a conservative substitution;

preferably, the VH of the antibody or antigen-binding fragment thereof comprises: VH CDR1 as shown in SEQ ID NO: 19, VH CDR2 as shown in SEQ ID NO: 20 and VH CDR3 as shown in SEQ ID NO: 21, and the VL of the antibody or antigen-binding fragment thereof comprises: VL CDR1 as shown in SEQ ID NO: 28, VL CDR2 as shown in SEQ ID NO: 29, and VL CDR3 as shown in SEQ ID NO: 30.

The anti-NGF antibody or antigen-binding fragment thereof capable of specifically binding to NGF according to the present invention, the antibody or antigen-binding fragment thereof comprising a heavy chain variable region and a light chain variable region, wherein, the heavy chain variable region comprises the three CDRs comprised in the heavy chain variable region as shown in any one of SEQ ID NOs: 1, 5 and 9; and the light chain variable region comprises the three CDRs comprised in the light chain variable region as shown in any one of SEQ ID Nos: 3, 7 and 11;

preferably, the three CDRs comprised in the heavy chain variable region and/or the three CDRs comprised in the light chain variable region are defined by the Kabat, Chothia or IMGT numbering systems.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 1;

(ii) sequence having a substitution, deletion or addition of one or more amino acids (e.g. a substitution, deletion or addition of 1, 2, 3, 4 or 5 amino acids) compared to SEQ ID NO: 1, or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO: 1; and/or, (b) a light chain variable region (VL) comprising amino acid sequence selected from:

(iv) sequence as shown in SEQ ID NO: 3;

(v) sequence having a substitution, deletion or addition of one or more amino acids (e.g. a substitution, deletion or addition of 1, 2, 3, 4 or 5 amino acids) compared to SEQ ID NO: 3, or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO: 3;

preferably, the substitution described in (ii) or (v) is a conservative substitution;

preferably, the antibody or antigen-binding fragment thereof comprises: VH having sequence as shown in SEQ ID NO: 1 and VL having sequence as shown in SEQ ID NO: 3.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 5;

(ii) sequence having a substitution, deletion or addition of one or more amino acids (e.g. a substitution, deletion or addition of 1, 2, 3, 4 or 5 amino acids) compared to SEQ ID NO: 5, or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO: 5; and/or, (b) a light chain variable region (VL) comprising amino acid sequence selected from:

(iv) sequence as shown in SEQ ID NO: 7;

(v) sequence having a substitution, deletion or addition of one or more amino acids (e.g. a substitution, deletion or addition of 1, 2, 3, 4 or 5 amino acids) compared to SEQ ID NO: 7, or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO: 7;

preferably, the substitution described in any one of (ii)-(v) is conservative substitution;

preferably, the antibody or antigen-binding fragment thereof comprises: VH having sequence as shown in SEQ ID NO: 5 and VL having sequence as shown in SEQ ID NO: 7.

The antibody or antigen-binding fragment thereof according to the present invention, wherein the antibody or antigen-binding fragment thereof comprises:

(a) a heavy chain variable region (VH) comprising amino acid sequence selected from:

(i) sequence as shown in SEQ ID NO: 9;

(ii) sequence having a substitution, deletion or addition of one or more amino acids (e.g. a substitution, deletion or addition of 1, 2, 3, 4 or 5 amino acids) compared to SEQ ID NO: 9, or (iii) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO: 9; and/or, (b) a light chain variable region (VL) comprising amino acid sequence selected from:

(iv) sequence as shown in SEQ ID NO: 11;

(v) sequence having a substitution, deletion or addition of one or more amino acids (e.g. a substitution, deletion or addition of 1, 2, 3, 4 or 5 amino acids) compared to SEQ ID NO: 11, or (vi) sequence having at least 80%, at least 85%, at least 90%, at least 91%, at least 92%, at least 93%, at least 94%, at least 95%, at least 96%, at least 97%, at least 98%, at least 99%, or 100% sequence identity to the sequence as shown in SEQ ID NO: 11;

preferably, the substitution described in any one of (ii)-(v) is conservative substitution;

preferably, the antibody or antigen-binding fragment thereof comprises: VH having sequence as shown in SEQ ID NO: 9 and VL having sequence as shown in SEQ ID NO: 11.

The antibody or antigen-binding fragment thereof according to the present invention, wherein the antibody or antigen-binding fragment thereof further comprises:

(a) a heavy chain constant region (CH) of human immunoglobulin or a variant thereof, the variant has a substitution, deletion or addition of one or more amino acids compared to the sequence from which it is derived (e.g., a substitution, deletion or addition of up to 20, up to 15, up to 10, or up to 5 amino acids; e.g., a substitution, deletion or addition of 1, 2, 3, 4 or 5 amino acids); and (b) a light chain constant region (CL) of human immunoglobulin or a variant thereof, the variant having a conservative substitution of up to 20 amino acids compared to the sequence from which it is derived (e.g. a conservative substitution of up to 15, up to 10, or up to 5 amino acids; e.g. a conservative substitution of 1, 2, 3, 4 or 5 amino acids);

preferably, the heavy chain constant region is IgG heavy chain constant region, such as IgG1, IgG2, IgG3 or IgG4 heavy chain constant region;

preferably, the light chain constant region is kappa light chain constant region.

The antibody or antigen-binding fragment thereof according to the present invention, wherein the antigen-binding fragment is selected from Fab, Fab', (Fab')₂, Fv, disulfide-linked Fv, scFv, diabody and single domain antibody (sdAb); and/or, the antibody is murine antibody, chimeric antibody, humanized antibody, bispecific antibody or multispecific antibody;

preferably, the humanized antibody or antigen-binding fragment thereof comprises: a heavy chain of the sequence as shown in any one of SEQ ID NOs: 33, 35, 37, 39, 43, 45, 47, 49, 51, 53, 55, 57, 59, 61 and 63, and/or a light chain of the sequence as shown in any one of SEQ ID Nos: 31 and 41.

The antibody or antigen-binding fragment thereof according to the present invention, wherein the antibody or antigen-binding fragment thereof is labeled; preferably, the antibody or antigen-binding fragment thereof is labeled with a detectable marker, such as enzyme (e.g. horseradish peroxidase), radioisotope, fluorescent dye, luminescent substance (such as chemiluminescent substance), or biotin.

The present invention also provides an isolated nucleic acid molecule encoding the antibody or antigen-binding fragment thereof, or the heavy chain variable region and/or light chain variable region thereof;

preferably, the polynucleotide comprises nucleotide coding sequence as shown in any one of SEQ ID NOs: 2, 4, 6, 8, 10, 12, 32, 34, 36, 38, 40, 42, 44, 46, 48, 50, 52, 54, 56, 58, 60, 62 and 64.

The present invention also provides a vector comprising the isolated nucleic acid molecule; preferably, the vector is a cloning vector or an expression vector.

The present invention also provides a host cell comprising the isolated nucleic acid molecule or the vector.

The present invention also provides a method for preparing the antibody or antigen-binding fragment thereof, comprising, culturing the host cell under conditions that allow the expression of the antibody or antigen-binding fragment thereof, and recovering the antibody or antigen-binding fragment thereof from the cultured host cell culture;

preferably, the host cell is mammalian cell, more preferably human, murine, sheep, horse, dog or cat cell, further preferably Chinese hamster ovary cell.

The present invention also provides a bispecific or multispecific molecule comprising the antibody or antigen-binding fragment thereof;

preferably, the bispecific or multispecific molecule specifically binds to NGF, and additionally specifically binds to one or more other targets;

preferably, the bispecific or multispecific molecule further comprises at least one molecule having a second binding specificity for a second target (e.g., a second antibody).

The present invention also provides an immunoconjugate comprising the antibody or antigen-binding fragment thereof and a therapeutic agent linked to the antibody or antigen-binding fragment thereof;

preferably, the therapeutic agent is selected from toxins, radioisotopes, drugs or cytotoxic agents;

preferably, the therapeutic agent is selected from the group consisting of alkylating agents, mitotic inhibitors, antitumor antibiotics, antimetabolites, topoisomerase inhibitors, tyrosine kinase inhibitors, radionuclide agents, and any combination thereof;

preferably, the immunoconjugate is an antibody-drug conjugate (ADC).

The present invention also provides a pharmaceutical composition, comprising the antibody or antigen-binding fragment thereof, bispecific or multispecific molecule or immunoconjugate, and a pharmaceutically acceptable carrier and/or excipient;

preferably, the pharmaceutical composition further comprises an additional pharmaceutically active agent;

preferably, the antibody or antigen-binding fragment thereof, bispecific or multispecific molecule or immunoconjugate is provided with the additional pharmaceutically active agent as separate components or as components of the same composition.

The present invention also provides a kit, comprising the antibody or antigen-binding fragment thereof;

preferably, the antibody or antigen-binding fragment thereof is labeled with a detectable marker, such as enzyme (e.g. horseradish peroxidase), radioisotope, fluorescent dye, luminescent substance (such as chemiluminescent substance), or biotin;

preferably, the kit further comprises a second antibody that specifically recognizes the antibody or antigen-binding fragment thereof;

preferably, the second antibody further comprises a detectable marker, such as enzyme (e.g. horseradish peroxidase), radioisotope, fluorescent dye, luminescent substance (such as chemiluminescent substance), or biotin.

The present invention also provides a chimeric antigen receptor, comprising an antigen-binding domain of the antibody or antigen-binding fragment thereof;

preferably, the antigen-binding domain comprises the heavy chain variable region and the light chain variable region of the antibody or antigen binding fragment thereof;

preferably, the antigen-binding domain is scFv;

preferably, the antigen binding receptor comprises an antigen-binding fragment of the antibody;

preferably, the antigen binding receptor is expressed by immune effector cells (e.g. T cells).

The present invention also provides the use of the antibody or antigen-binding fragment thereof, or the bispecific or multispecific molecule, or the immunoconjugate, or the pharmaceutical composition, or the chimeric antigen receptor, in the preparation of a medicament, wherein the medicament is for the treatment of NGF-mediated diseases or disorders;

preferably, the disease or disorder includes osteoarthritic pain, postoperative pain, rheumatoid arthritic pain, low back pain, cancer-related pain, neuropathic pain, and visceral pain;

preferably, the subject is mammal, such as human.

The present invention also provides a method for preventing and/or treating a disease in a subject (e.g., human), the method comprising administering to a subject in need thereof an effective amount of the antibody or antigen binding fragment thereof, or the bispecific or multispecific molecule, or the immunoconjugate, or the pharmaceutical composition, or the chimeric antigen receptor, or the host cell;

the disease is NGF-mediated disease or disorder;

preferably, the disease or disorder includes osteoarthritic pain, postoperative pain, rheumatoid arthritic pain, low back pain, cancer-related pain, neuropathic pain, and visceral pain;

preferably, the subject is mammal, such as human.

The present invention also provides a method of detecting the presence or amount of NGF (e.g., human NGF) in a sample, comprising the steps of:

(1) contacting the sample with the antibody or antigen-binding fragment thereof;

(2) detecting the formation of a complex by the antibody or antigen-binding fragment thereof and NGF, or detecting the amount of the complex;

preferably, the antibody or antigen-binding fragment thereof is labeled with a detectable marker;

preferably, the NGF is human NGF.

The inventors found that the antibodies or antigen-binding fragments thereof provided by the present invention have the following advantages:

1. The antibodies provided by the present invention have high affinity, and the affinity constant $K_D$ value is less than or close to $10^{-12}$M, which can effectively block the binding of NGF to its receptors and block the pain response;

2. The antibodies provided by the present invention have extremely strong specificity for the binding to the antigen, without cross-binding to NGF homo-family proteins, and a reduced clinical safety risk can be expected;

3. The antibodies provided by the present invention have significantly analgesic effects in animals, and the expected clinical effects are significant;

4. The antibodies provided by the invention are expressed by CHO cells, and have the advantages of high yield, high activity, simple purification process and low production cost.

DESCRIPTION OF DRAWINGS

FIG. 1 shows the ELISA results of the anti-NGF antibody of the present invention binds to human NGF protein.

FIGS. 2A-2C show the effects of the anti-NGF antibody of the present invention on the binding of human NGF to receptors TrkA and p75.

FIG. 5 shows that the anti-NGF antibody of the present invention inhibits the reporter gene expression in TrkA/NFAT-bla/CHO cells.

FIGS. 6A-6E show that the anti-NGF antibody of the present invention specifically binds to NGF and inhibits NGF-induced signaling pathway.

FIGS. 8A-8E show the effects of the anti-NGF antibody 43E5 and 138E12 of the present invention on CFA-induced inflammatory pain in mice, wherein P<0.01 vs normal saline; *P<0.001 vs normal saline.

DETAILED DESCRIPTION OF THE INVENTION

Figure 2C:
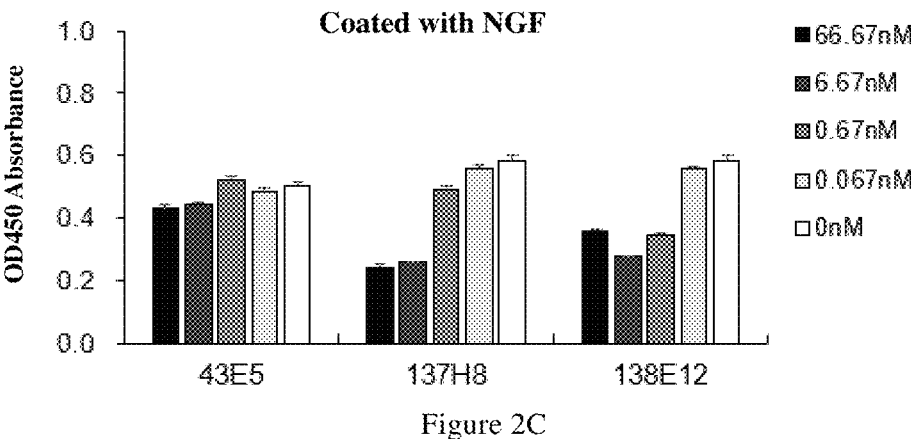

The following description of the application is merely illustrative of various embodiments of the application. Therefore, the specific modifications discussed herein should not be construed as limitations on the scope of the application. Various equivalents, changes and modifications can be easily made by those skilled in the art without departing from the scope of the present application, and it should be understood that such equivalent embodiments are included within the scope of the present invention. All documents, including publications, patents, and patent applications, cited in this application are incorporated by reference in their entirety.

In some embodiments, the antibodies or antigen-binding fragments described herein are capable of specifically binding to NGF with a binding affinity ($K_D$) of less than or close to $10^{-12}$M, as measured by Biolayer Optical Interferometry. The binding affinity value can be expressed as $K_D$ value, which is calculated by the ratio of off-rate to on-rate ($k_{off}/k_{on}$) when the binding of an antigen to antibody reaches equilibrium. The antigen binding affinity (e.g. $K_D$) may suitably be determined by suitable methods known in the art, including, for example, Fortebio's Biolayer Optical Interferometry by using an instrument.

In certain embodiments, the antibodies or antigen-binding fragments described herein bind to NGF with an EC50 (i.e., half binding concentration) of 0.1 nM. Binding of an antibody or antigen-binding fragment to NGF can be determined by methods known in the art, such as sandwich assays such as ELISA, Western blot, FACS or other binding assays.

The antibodies are specific for NGF. In certain embodiments, the antibodies optionally do not bind to NGF homo-family proteins Brain-Derived Neurotrophic Factor (BDNF), Neurotrophic factor-3 (NT-3), Neurotrophic factor-4 (NT-4).

Example 1: Preparation of Murine Anti-NGF Antibody

As an immunogen, recombinant human NGF protein (Beijing Yiqiao Shenzhou Technology Co., Ltd., 11050-HNAC) was mixed and emulsified with an equal volume of Freund's complete adjuvant (Sigma-Alderich, F5881) for initial immunization. Five 6-week-old BALB/c and C57 mice (Jiangsu Huafukang) were prepared, and each animal was injected subcutaneously with 50 μg Immunogen (excluding the weight of the adjuvant, the same hereafter). The immunogen was mixed and emulsified with incomplete Freund's adjuvant (Sigma-Alderich, F5506) for subsequent booster immunizations. Two weeks after the initial immunization, each animal was injected intraperitoneally with 25 μg immunogen for the first booster; 2 weeks later, each animal was injected subcutaneously with 25 μg immunogen for the second booster. 4-5 weeks later, 25 μg of immunogen was injected intraperitoneally for the last immunization shock.

After the last immunization, Mouse B cells were isolated, mixed with SP2/0 cells (Cell Bank of Chinese Academy of Sciences, TCM18), and fused according to the operation manual of the Electroporator of BTX company. The fusion cells were cultured, and then screened for hybridoma cells that could bind to NGF and inhibit the binding of human NGF to receptor TrkA by Enzyme Linked Immunosorbent Assay (ELISA). Subcloning was performed by limiting dilution method, and 3 positive hybridoma monoclonal cell lines were obtained by screening with the same ELISA method, which were named 43E5, 137H8 and 138E12 respectively.

The hybridoma monoclonal cell lines were expanded and cultured with serum-free medium, and the medium was collected and purified by protein G column to obtain murine anti-human NGF monoclonal antibodies 43E5, 137H8, and 138E12.

Example 2: ELISA Detection of the Binding of Murine Anti-NGF Antibody to Human NGF The binding capacity of anti-NGF antibodies was investigated by using human NGF as an antigen (Beijing Yiqiao Shenzhou Technology Co., Ltd., 11050-HNAC). Each well of a 96-well microtiter plate was coated with 50 ng of human NGF, after washing and blocking, and then added with serially diluted antibodies, and incubated at room temperature for 1 hour. After washing three times, HRP-conjugated goat anti-mouse antibody (Biolegend, 405306) was added and incubated at room temperature for 1 hour. After washing three times, tetramethylbenzidine (TMB, Biolegend, 421101) was added for color development. 1M HCl was used to terminate the color development, and the absorbance values were read at 450 nm with a microplate reader.

All the anti-NGF antibodies secreted by the three hybridomas bound to human NGF in a dose-dependent (FIG. 1), and the EC50 of the three antibodies for binding to human NGF were 0.082 nM, 0.112 nM, and 0.1 nM, respectively (Table 1).

TABLE 1

| EC50 of anti-NGF antibody binding to human NGF | | | |
| --- | --- | --- | --- |
| Antibody | 43E5 | 137H8 | 138E12 |
| EC50 (nM) | 0.082 | 0.112 | 0.100 |

Example 3: Binding Affinity Assay of Murine Anti-NGF Antibody to Human NGF

The affinities of the antibodies were detected with Bio-molecular Interaction Detection Platform (ForteBio Octet Red96 (PALL)). Biotin-labeled human NGF was immobilized by using SA (Streptavidin) Biosensor (Fortebio, 18-5021), and then conjugated with gradient concentrations of anti-NGF antibodies. Buffer (1× Kinetics Buffer: PBS+ 0.1% BSA+0.05% Tween20) was added for dissociation, and finally the affinity kinetic constant of antigen-antibody binding was calculated by instrument algorithm (Table 2).

TABLE 2

| Binding Affinity of anti-NGF antibody to human NGF | | | |
| --- | --- | --- | --- |
| Antibody | Affinity Constant $K_D$ (M) | Binding Constant $K_{on}$ (1/Ms) | Dissociation Constant $k_{dis}$ (1/s) |
| 43E5 | <1.0E−12 | 3.73E+05 | <1.0E−07 |
| 137H8 | 3.81E−10 | 1.29E+05 | 4.91E−05 |
| 138E12 | <1.0E−12 | 6.34E+05 | <1.0E−07 |

Example 4: Detection of the Blocking Effect of Murine Anti-NGF Antibody on the Binding of Human NGF to Receptor TrkA or p75

A. Blocking effect of anti-NGF antibody on the binding of human NGF to receptor TrkA If the method of coated receptor TrkA is used for detection, 50 ng of NGF receptor TrkA protein (fused to human Fc) was coated in each well of a 96-well microtiter plate, washed three times, and then blocked with 3% BSA for 1 hour. 10000 ng/mL (66.67 nM) anti-NGF antibody was 3-fold serially diluted for 10 times to 0.17 ng/mL (0.0011 nM). 100 μl was taken and mixed with an equal volume of 1 μg/mL biotin-labeled human NGF, incubated at room temperature for 0.5 hours, and then added to an ELISA plate which has been washed with blocking solution. Incubated for 1 hour at room temperature and washed three times. Streptavidin-labeled HRP (Biolegend, 405210) was added, and incubated for 0.5 h and then washed three times. The microtiter plate was added with TMB, and read after the color development was terminated.

If using the coated ligand NGF method for detection, each well of a 96-well microtiter plate was coated with 50 ng of human NGF and washed three times. After blocking with 3% BSA for 1 hour, washed three times, 10000 ng/mL (66.67 nM) anti-human NGF antibody was 3-fold diluted to 0.17 ng/mL (0.0011 nM), 100 μL was added to each well, incubated at room temperature for 1 hour, and then washed three times. 100 μL of 1 μg/mL TrkA fused to human Fc was added to each well, incubated for 1 hour at room temperature, and washed three times. HRP-conjugated donkey anti-human IgG antibody (Biolegend, 410902) was added and reacted for 1-hour at room temperature. After washing, add TMB to develop color, and read after the termination of development.

The results are shown in FIG. 2A and FIG. 2B, the anti-NGF antibodies can block the binding of human NGF to the receptor TrkA, and the blocking effect increases significantly with the increase of the antibody concentration. The IC50 values of the three antibodies blocking the binding of human NGF to the receptor TrkA are shown in Table 3 and Table 4:

TABLE 3

| Blocking TrkA-NGF binding IC50 | | | |
|---|---|---|---|
| Antibody | 43E5 | 137H8 | 138E12 |
| IC50 (nM) | 0.767 | 0.738 | 0.677 |

TABLE 4

| Blocking NGF-TrkA binding IC50 | | | |
|---|---|---|---|
| Antibody | 43E5 | 137H8 | 138E12 |
| IC50 (nM) | 0.967 | 0.791 | 0.865 |

B. Blocking Effect of Anti-NGF Antibody on the Binding of Human NGF to Receptor p75

Each well of a 96-well microtiter plate was coated with 50 ng of human NGF, blocked with 3% BSA for 1 h, washed 3 times, and added with 10 µg/mL, 1 µg/mL, 0.1 µg/mL, 0.01 µg/mL and 0 µg/mL (66.67 nM, 6.67 nM, 0.67 nM, 0.067 nM and 0 nM) anti-NGF antibody 40 µL, and incubated at room temperature for 15 minutes. 40 µL of 2 µg/mL p75 fused to human Fc (Beijing Yiqiao Shenzhou Technology Co., Ltd., 13184-H02H) was added to each well, incubated for 1 hour and then washed 3 times. 100 µL HRP-conjugated donkey anti-human Fc secondary antibody (Biolegend, 410902) was added and reacted for 1-hour at room temperature. After washing, added TMB to develop color, and read after the termination of development. As shown in FIG. 2C, among the three anti-NGF antibodies selected, 43E5 can not block the binding of human NGF to the receptor p75, whereas 137H8 and 138E12 can block the binding of human NGF to the receptor p75.

It should be noted that during the clinical trial of Pfizer/Lilly's NGF antibody Tanezumab, the adverse effect of Rapidly Progressive Osteoarthritis (RPOA) was observed. Tanezumab can simultaneously block the binding of NGF to TrkA and p75. Studies have shown that p75 receptor function is associated with neuron development, osteoblast differentiation, proliferation, myoblast differentiation, muscle repair, and the like (Akiyama Y et al. (2014) Differentiation, 87:111-118; Deponti et al. (2009) Molecular Biology of the Cell, 20:3620-3627; Mikami et al. (2012) Differentiation, 84:392-399). In addition, GZ389988A, a small molecule inhibitor of TrkA developed by Sanofi, did not exhibit adverse effect of RPOA during the clinical trial, which was believed to be associated with the selective effect of GZ389988A on TrkA while retaining the complete function of the NGF-p75 pathway (Krupka et al. (2019) Osteoarthritis and Cartilage, 27:1599-1607). In the present invention, 43E5 cannot block the binding of human NGF to p'75, thus, it is expected to have a less possibility to exhibit RPOA in clinic, and have a safety superior to other antibodies with p75 blocking effect.

Example 5: In Vitro Neutralization Activity Detection of Murine Anti-NGF Antibody A. NGF-Induced Proliferation of TF-1 Cell The growth of TF-1 cells (human blood leukemia cells, ATCC, CRL-2003) is highly dependent on GM-CSF (Granulocyte-Macrophage Colony-Stimulating Factor). However, NGF can also induce the growth of TF-1 cells after binding to TrkA on the surface of TF-1 cells, so it does not need to rely on GM-CSF.

TF-1 cells were cultured in RPMI 1640 culture medium (HyClone, SH30027) containing 10% FBS (Gibco, 10091148) and 2 µg/mL GM-CSF (R&D, 215-GM-010), and cells were collected in logarithmic growth phase, and washed thoroughly to remove the GM-CSF in the original medium. Resuspended in medium without GM-CSF, and 5000 cells per well were diluted in 80 µl medium and plated onto the white transparent bottom 96-well cell culture plate (Corning, 3610). Anti-NGF antibody was 4-fold serially diluted, from 400 µg/mL (2666.67 nM) to prepare 10 concentrations, mixed with an equal volume of 50 ng/mL human NGF, incubated for 0.5 hours, and 20 µL was added to cells in the 96-well plate. After incubating in an incubator at 37° C., 5% $CO_2$ for 72 hours, 100 µL of CellTiter-Glo® Cell Viability Detection Reagent (Promega, G7573) was added, and the cells were shaken and disrupted. Optical luminescence signals were then read by using a Multimode Reader (SpectraMax).

Figure 3:
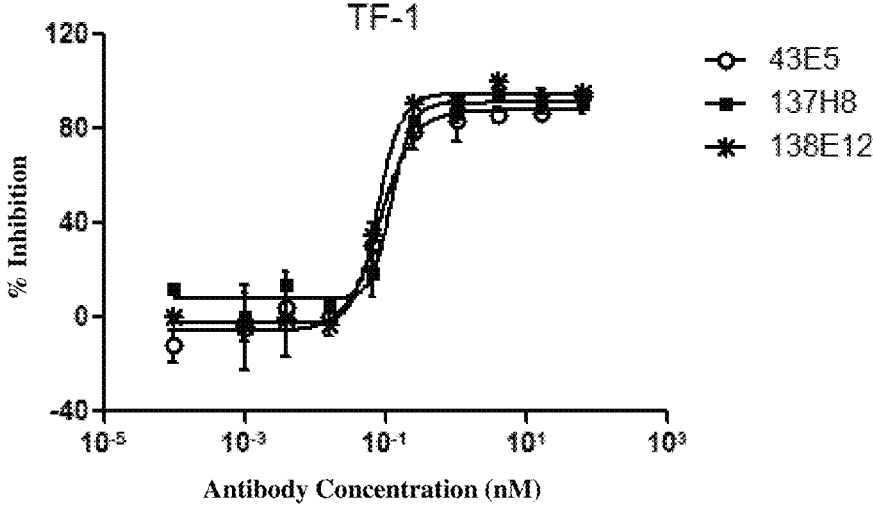
FIG. 3 shows that the anti-NGF antibody of the present invention inhibits NGF-induced proliferation of TF-1 cell.

As shown in FIG. 3, all the three anti-NGF antibodies are capable of inhibiting the proliferation of TF-1 cells induced by human NGF, and the IC50 values are shown in Table 5.

TABLE 5

| Anti-NGF antibodies inhibiting NGF-induced proliferation of TF-1 cell IC50 | | | |
|---|---|---|---|
| Antibody | 43E5 | 137H8 | 138E12 |
| IC50 (nM) | 0.083 | 0.123 | 0.077 |

B. Assay of NGF-Induced Proliferation of TrkA/Ba/F3 Cells

The growth of Ba/F3 cells involves two pathways: IL3-dependent and IL3-independent. The IL3-independent growth requires Ba/F3 cells to stably express active kinases. Ba/F3 cells expressing full-length human TrkA (TrkA/Ba/F3) were constructed, and the proliferation of such cells requires the addition of NGF for induction.

TrkA/Ba/F3 cells were cultured in RPMI 1640 culture medium containing 10% FBS and 100 ng/mL NGF. The cells were collected and washed thoroughly to remove NGF in the original growth medium, 3000 cells per well were resuspended in 80 µL of NGF-free medium and plated on the white transparent bottom 96-well cell culture plate (Corning, 3610). The human NGF was mixed with serially diluted antibody and added to the cells in a 96-well plate. The final concentration of NGF was 5 ng/mL, and the final concentration of serially diluted anti-NGF antibody was up to 40 µg/mL (266.67 nM). After incubating cells in an incubator at 37° C., 5% $CO_2$ for 48 hours, CellTiter-Glo® Cell Viability Detection Reagent (Promega, G7573) was added, and the cells were shaken and disrupted. Optical luminescence signals were then read by using a Multimode Reader (SpectraMax).

Figure 4:
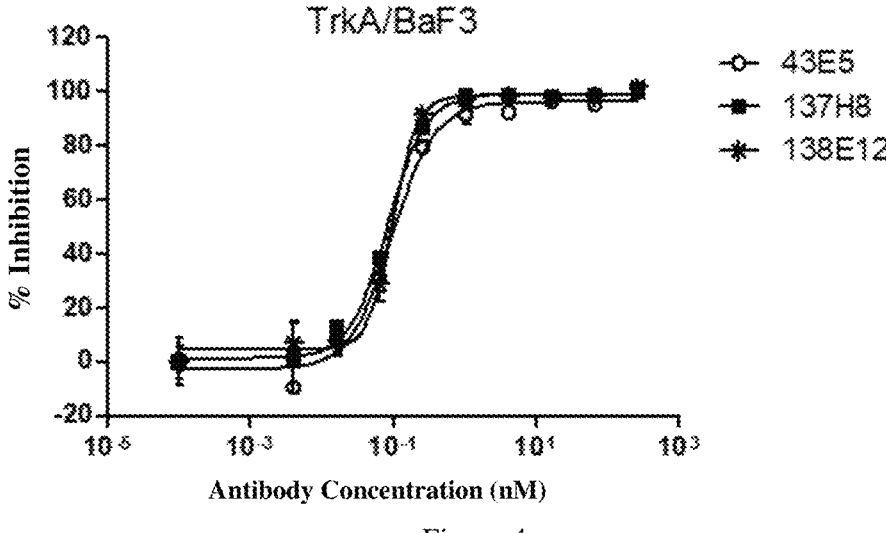
FIG. 4 shows that the anti-NGF antibody of the present invention inhibits NGF-induced proliferation of TrkA/Ba/F3 cell.

During the process of observing the growth of TrkA/Ba/F3 cells, the cells added with human NGF can proliferate normally; the three anti-NFG antibodies can inhibit the proliferation of TrkA/Ba/F3 cells induced by NGF, and the inhibitory effect was increased with the increase of the concentration (FIG. 4). IC50 values are as shown in Table 6.

TABLE 6

| Anti-NGF antibodies inhibiting NGF-induced proliferation of TrkA/Ba/F3 cells IC50 | | | |
|---|---|---|---|
| Antibody | 43E5 | 137H8 | 138E12 |
| IC50 (nM) | 0.096 | 0.083 | 0.098 |

C. Detection of Reporter Gene Expression Induced by NGF in TrkA/NFAT-Bla/CHO Cells The binding of NGF to the transmembrane receptor TrkA can activate the downstream phospholipase C (PLC), which leads to the increase of intracellular calcium concentration and the activation of protein kinase C (PKC) through a series of signaling transduction, and finally promotes the transportation of the nuclear factor and activated T cell nuclear factor (NFAT) from the cytoplasm to the nucleus, thereby initiating the expression of NFAT-dependent gene. The gene encoding human TrkA is integrated into the genome of TrkA/NFAT-bla/CHO cells (ThermoFisher, K1516), and an NFAT response element is inserted upstream of the reporter gene β-lactamase (β-bla) gene. When the NGF-TrkA pathway is activated, the cells will express β-lactamase under the control of NFAT, and the activity of β-lactamase can reflect the degree of the activation of the NGF-TrkA pathway.

TrkA-NFAT-bla/CHO cells were prepared according to the manufacturer's instructions, and 10,000 cells per well were plated into a 384-well plate and cultured overnight. The human NGF was mixed with serially diluted antibody, incubate at room temperature for 0.5 h, and then add them to the cells, so that the final action concentration of NGF was 80 ng/mL. The final concentration of serially diluted NGF antibody was up to 40 μg/mL (266.67 nM). After culturing for 5 hours in an incubator at 37° C., 5% $CO_2$, LiveBLAzer™ FRET-B/G β-lactamase substrate CCF4 (ThermoFisher, K1095) prepared according to the manual was added to the cells, and kept in the dark at room temperature for 2 hours. Read the signal by a Multimode Reader (SpectraMax).

The results show that all the three anti-NGF antibodies can inhibit the activation of human NGF-triggered signaling pathway (FIG. 5), and the IC50 values are shown in Table 7.

TABLE 7

| Anti-NGF antibodies inhibiting reporter gene expression in TrkA/NFAT-bla/CHO cells IC50 | | | |
|---|---|---|---|
| Antibody | 43E5 | 137H8 | 138E12 |
| EC50 (nM) | 0.0532 | 0.0859 | 0.0442 |

Example 6: Detection of Anti-NGF Antibody Specificity

A. ELISA Detection of Murine Anti-NGF Antibody Binding to NGF Homo-Family Proteins Each well of a 96-well microtiter plate was coated with 50 ng of human NGF (Beijing Yiqiao Shenzhou Technology Co., Ltd., 11050-HNAC), human BDNF (Beijing Yiqiao Shenzhou Technology Co., Ltd., 50240-MNAS), human NT-3 (Beijing Yiqiao Shenzhou Technology Co., Ltd., 10286-HNAE), or human NT-4 (Alomone, N-270). The bindings of the murine anti-NGF antibodies to human NGF and three homo-family proteins were detected according to the method described in Example 2.

Figure 6C:
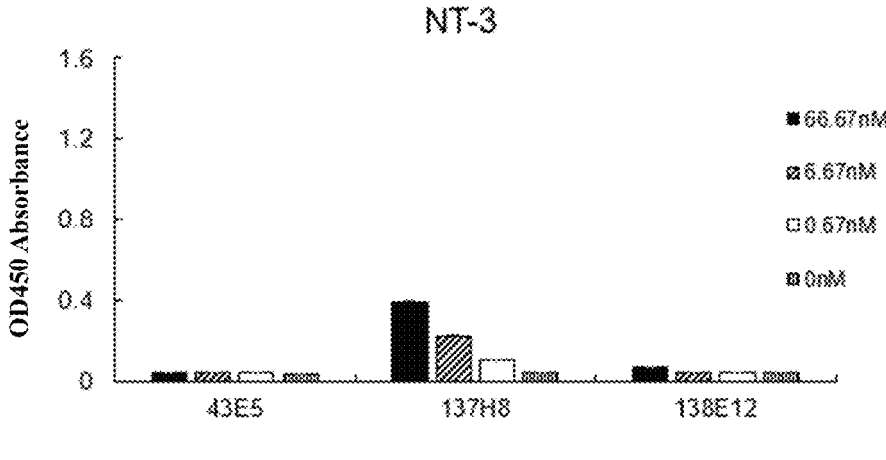
Figure 6D:
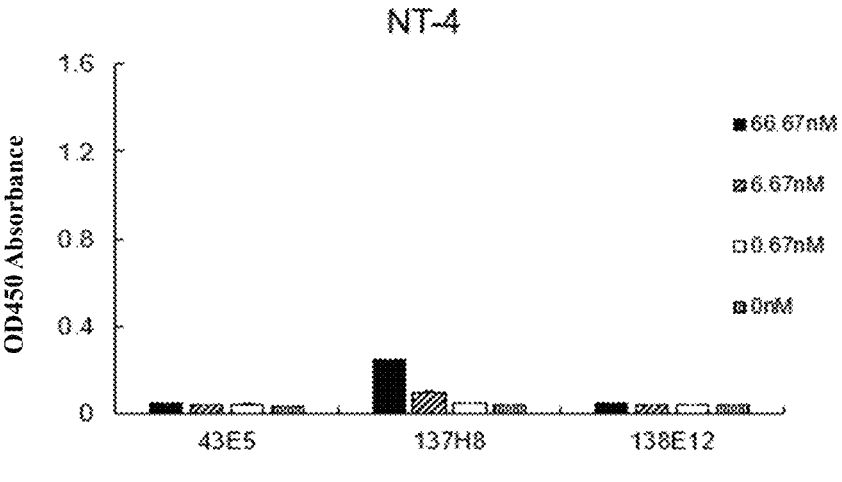

As shown in FIGS. 6A-6D, the three murine anti-NGF antibodies have high affinity to NGF (FIG. 6A), and antibodies 43E5 and 138E12 do not substantially bind to BDNF (FIG. 6B), NT-3 (FIG. 6C), and NT-4 (FIG. 6D). Antibody 137H8 binds weakly to the three NGF homo-family proteins (FIGS. 6B-6D).

B. Murine Anti-NGF Antibody Specifically Inhibits Reporter Gene Expression in TrkA-NFAT-bla/CHO Cells As in Example 5C, TrkA-NFAT-bla/CHO cells, TrkB-NFAT-bla/CHO cells (ThermoFisher, K1491) and TrkC-NFAT-bla/CHO cells (ThermoFisher, K1515) were prepared according to the manufacturer's instruction.

The antibodies of the present invention were diluted to 40 μg/mL (266.67 nM), and mixed with human NGF or human BDNF (for TrkB-NFAT-bla/CHO cells), or human NT-3 (for TrkC-NFAT-bla/CHO cells) and incubated at room temperature for 0.5 h before adding to the cells. After 5 hours of incubation, LiveBLAzer™ FRET-BIG β-lactamase substrate CCF4 prepared according to the manual was added to the cells, and kept in the dark at room temperature for 2 hours. The signals were read by a Multimode Reader.

Figure 6E:
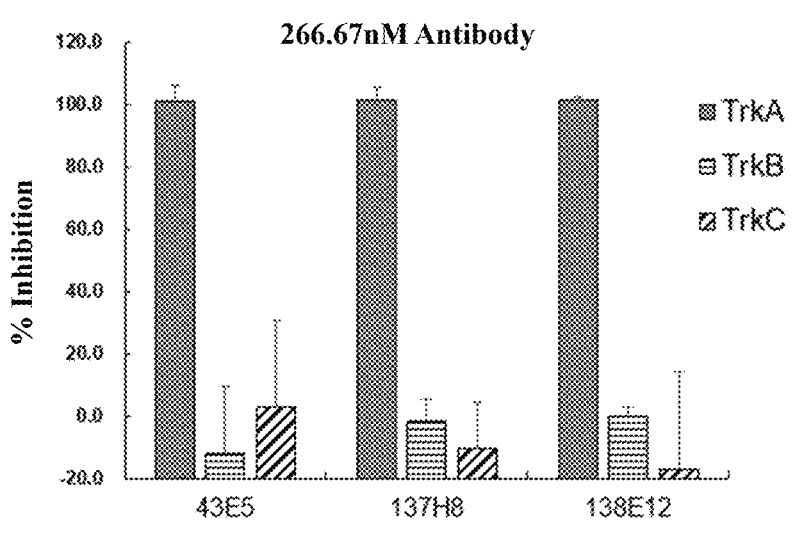
Figure 7:
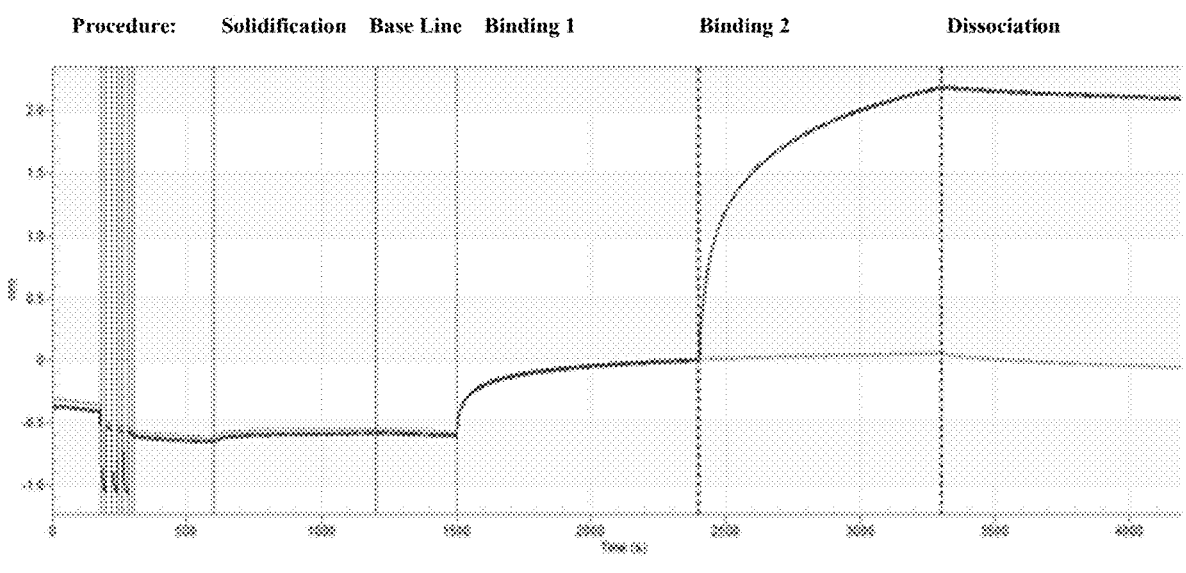
FIG. 7 shows competitive binding curve of the anti-NGF antibody 43E5 and 138E12 of the present invention.

The three anti-NGF antibodies can inhibit the subsequent signaling caused by the binding of NGF to TrkA, without affecting the signaling of BDNF and TrkB, and NT-3 and TrkC (FIG. 6E);

It should be noted that, compared to Pfizer/Lilly's NGF antibody Tanezumab, the three anti-NGF antibodies of the present application, especially the antibodies 43E5 and 138E12, do not bind to the NGF homo-family antibodies, i.e., BDNF, NT-3, and NT-4, whereas Tanezumab exhibits obviously cross-binding effect on NT-3 and NT-4, that is, the specificity of 43E5 and 138E12 of the present application is better than that of Tanezumab, and the expected clinical adverse reaction is better than that of Tanezumab.

Example 7: Epitope Grading of Anti-NGF Antibodies 43E5 and 138E12

Whether the two anti-NGF antibodies 43E5 and 138E12 competitively bind to NGF was determined by using the biomolecular interaction detection platform Fortebio Ocete RED96. Biotin-labeled human NGF was immobilized by SA (Streptavidin) Biosensor. The first loading step was to monitor the binding of antibody 138E12. The second loading step was to continue to monitor the binding of 138E12 or 43E5. Finally, buffer (1× Kinetics Buffer: PBS+0.1% BSA+0.05% Tween 20) was added for dissociation.

As shown in FIG. 7, 43E5 and 138E12 can bind to human NGF simultaneously in a non-competitive manner.

Example 8: Sequencing and Sequence Analysis of Variable Region of Murine Anti-NGF Antibody Total RNA of hybridoma cells was extracted by using TRIzol kit (Ambion, 15596-026), and was used as a template to synthesize the first-strand cDNA (Takara). The antibody light chain and heavy chain fragments were obtained by rapid amplification of cDNA ends (RACE), and the amplified fragments were cloned into standard vectors respectively. After sequencing, the sequences of the heavy chain and light chain variable regions of the anti-NGF antibodies 43E5, 137H8, and 138E12 obtained are as follows:

Anti-NGF antibody 43E5:
```
                                        (SEQ ID NO: 1)
Amino acid sequence of the heavy chain variable
region:
QVQLQQSGAELVRPGASVTLSCKASGYTFTDYEMHWVRQTPVHGLEWIG

AIDPETGGTAYNQKFKGKATLTADKSSSTAYMELRSLTSEDSAVYYCRR

GANLNHYGNDEGSYWGQGTLVTVSA

Nucleic acid sequence of the heavy chain variable
region:
                                        (SEQ ID NO: 2)
CAGGTTCAACTGCAGCAGTCTGGGGCTGAGCTGGTGAGGCCTGGGGCTT

CAGTGACGCTGTCCTGCAAGGCTTCGGGCTACACATTTACTGACTATGA

AATGCACTGGGTGAGGCAGACACCTGTGCATGGCCTGGAATGGATTGGA

GCTATTGATCCTGAAACTGGTGGTACTGCCTACAATCAGAAGTTCAAGG

GCAAGGCCACACTGACTGCAGACAAATCCTCCAGCACAGCCTACATGGA

GCTCCGCAGCCTGACATCTGAGGACTCTGCCGTCTATTACTGTAGAAGA

GGGGCAAATCTTAATCACTATGGTAACGACGAGGGTTCTTACTGGGGCC

AAGGGACTCTGGTCACTGTCTCTGCA

Amino acid sequence of the light chain variable
region:
                                        (SEQ ID NO: 3)
DVVMTQTPLTLSVTIGQPASISCKSSQSLLHSVGKTYLNWLLQRPGQSP

KRLIYLVSKLDSGVPDRFTGSGSGTDFTLKISRVEAEDLGVYFCWQGTH

LPQTFGGGTKLEIK

Nucleic acid sequence of the light chain variable
region:
                                        (SEQ ID NO: 4)
GATGTTGTGATGACCCAGACTCCACTCACTTTGTCGGTTACCATTGGAC

AACCAGCCTCCATCTCTTGTAAGTCAAGTCAGAGCCTCTTACATAGTGT

TGGAAAGACATATTTGAATTGGTTGTTACAGAGGCCAGGCCAGTCTCCA

AAGCGCCTAATCTATCTGGTGTCTAAACTGGACTCTGGAGTCCCTGACA

GGTTCACTGGCAGTGGATCAGGGACAGATTTCACACTGAAAATCAGCAG

AGTGGAGGCTGAGGATTTGGGAGTTTATTTTTGCTGGCAAGGTACACAT

CTTCCTCAGACGTTCGGTGGAGGCACCAAGCTGGAAATCAAA

Anti-NGF antibody 137H8:
Amino acid sequence of the heavy chain variable
region:
                                        (SEQ ID NO: 5)
QVQLKESGPGLVAPSQSLSITCTVSGFSLTGYAVNWVRQPPGKGLEWLG

MIWFDGSTDYNSALKSRLSISKDNSKSQVFLKMNSLQTDDTARYYCARD

YYGSSWYFDVWGAGTTVTVSS

Nucleic acid sequence of the heavy chain variable
region:
                                        (SEQ ID NO: 6)
CAGGTGCAGCTGAAGGAGTCAGGACCTGGCCTGGTGGCGCCCTCACAGA

GCCTGTCCATCACATGCACCGTCTCAGGGTTCTCATTAACCGGCTATGC

TGTAAACTGGGTTCGCCAGCCTCCAGGAAAGGGTCTGGAGTGGCTGGGA

ATGATATGGTTTGATGGAAGCACAGACTATAATTCAGCTCTCAAATCCA
```

```
GACTGAGCATCAGCAAGGACAACTCCAAGAGCCAAGTTTTCTTAAAAAT

GAACAGTCTGCAAACTGATGACACAGCCAGGTACTACTGTGCCAGAGAC

TACTACGGTAGTAGCTGGTACTTCGATGTCTGGGGCGCAGGGACCACGG

TCACCGTCTCCTCA

Amino acid sequence of the light chain variable
region:
                                        (SEQ ID NO: 7)
DIQMTQTTSSLSASLGDRVTISCRASQDISYYLNWYQQKPDGTVKLLIY

YTSRLHSGVPSRFSGSGSGTDYSLTISNLEQEDIATYFCQQGNTLPRTF

GGGTKLDIK

Nucleic acid sequence of the light chain variable
region:
                                        (SEQ ID NO: 8)
GATATCCAGATGACACAGACTACATCCTCCCTGTCTGCCTCTCTGGGAG

ACAGAGTCACCATCAGTTGCAGGGCAAGTCAGGACATTAGCTATTATTT

AAACTGGTATCAGCAGAAACCAGATGGAACTGTTAAACTCCTGATCTAC

TACACATCAAGATTACACTCAGGAGTCCCATCAAGGTTCAGTGGCAGTG

GGTCTGGAACAGATTATTCTCTCACCATTAGCAACCTGGAGCAAGAAGA

TATTGCCACTTACTTTTGCCAACAGGGTAATACGCTTCCTCGGACGTTC

GGTGGAGGCACCAAGCTGGACATCAAA

Anti-NGF antibody 138E12:
Amino acid sequence of the heavy chain variable
region:
                                        (SEQ ID NO: 9)
QVQLKESGPGLVAPSQSLSITCTVSGFSLTGYGVNWVRQPPGKGLEWLG

MIWFDGSTDYNSALKSRLSISKDNSKSQVFLKMNSLQTDDTARYYCARE

GYYYGTTYYFDYWGQGTTLTVSS

Nucleic acid sequence of the heavy chain variable
region:
                                        (SEQ ID NO: 10)
CAGGTGCAGCTGAAGGAGTCAGGACCTGGCCTGGTGGCGCCCTCACAGA

GCCTGTCCATCACATGCACCGTCTCAGGGTTCTCATTAACCGGCTATGG

TGTAAACTGGGTTCGCCAGCCTCCAGGAAAGGGTCTGGAGTGGCTGGGA

ATGATATGGTTTGATGGAAGCACAGACTATAATTCAGCTCTCAAATCCA

GACTGAGCATCAGCAAGGACAACTCCAAGAGCCAAGTTTTCTTAAAAAT

GAACAGTCTGCAAACTGATGACACAGCCAGGTACTACTGTGCCAGAGAG

GGTTATTACTACGGTACTACCTACTACTTTGACTACTGGGGCCAAGGCA

CCACTCTCACAGTCTCCTCA

Amino acid sequence of the light chain variable
region:
                                        (SEQ ID NO: 11)
DIQMTQTTSSLSASLGDRVTISCRASQDISNYLNWYQQKPDGTVKLLIY

YTSRLHSGVPSRFSGSGSGTDYSLTISNLEQEDIATYFCQQGNTLPRTF

GGGTKLEIK

Nucleic acid sequence of the light chain variable
region:
                                        (SEQ ID NO: 12)
GATATCCAGATGACACAGACTACATCCTCCCTGTCTGCCTCTCTGGGAG

ACAGAGTCACCATCAGTTGCAGGGCAAGTCAGGACATTAGCAATTATTT

AAACTGGTATCAGCAGAAACCAGATGGAACTGTTAAACTCCTGATCTAC
```

-continued
TACACATCAAGATTACACTCAGGAGTCCCATCAAGGTTCAGTGGCAGTG

GGTCTGGAACAGATTATTCTCTCACCATTAGCAACCTGGAGCAAGAAGA

TATTGCCACTTACTTTTGCCAACAGGGTAATACGCTTCCTCGGACGTTC

GGTGGAGGCACCAAGCTGGAAATCAAA

The CDRs defined by the Kabat and IMGT systems were obtained by sequence analysis. The following table (Table 8) lists the CDRs of the three anti-NGF antibodies based on the definitions by the Kabat and IMGT systems.

TABLE 8

Definition of antibody CDR

Antibody heavy chain CDR: CDR defined according to Kabat system is shown in black and bold; CDR defined by IMGT is underlined.

| Clone No. | CDR-H1 | SEQ ID No. | CDR-H2 | SEQ ID No. | CDR-H3 | SEQ ID No. |
|---|---|---|---|---|---|---|
| 43E5 | GYTFTDYEMH | 13 | AIDPETGGTAYNQKFKG | 14 | RRGANLNHYGNDEGSY | 15 |
| 137H8 | GFSLTGYAVN | 16 | MIWFDGSTDYNSALKS | 17 | ARDYYGSSWYFDV | 18 |
| 138E12 | GFSLTGYGVN | 19 | MIWFDGSTDYNSALKS | 20 | AREGYYYGTTYYFDY | 21 |

Antibody light chain CDR: CDR defined according to Kabat system is shown in black and bold; CDR defined by IMGT is underlined.

| Clone No. | CDR-L1 | SEQ ID No. | CDR-L2 | SEQ ID No. | CDR-L3 | SEQ ID No. |
|---|---|---|---|---|---|---|
| 43E5 | KSSQSLLHSVGKTYLN | 22 | LVSKLDS | 23 | WQGTHLPQT | 24 |
| 137H8 | RASQDISYYLN | 25 | YTSRLHS | 26 | QQGNTLPRT | 27 |
| 138E12 | RASQDISNYLN | 28 | YTSRLHS | 29 | QQGNTLPRT | 30 |

Figure 8A:
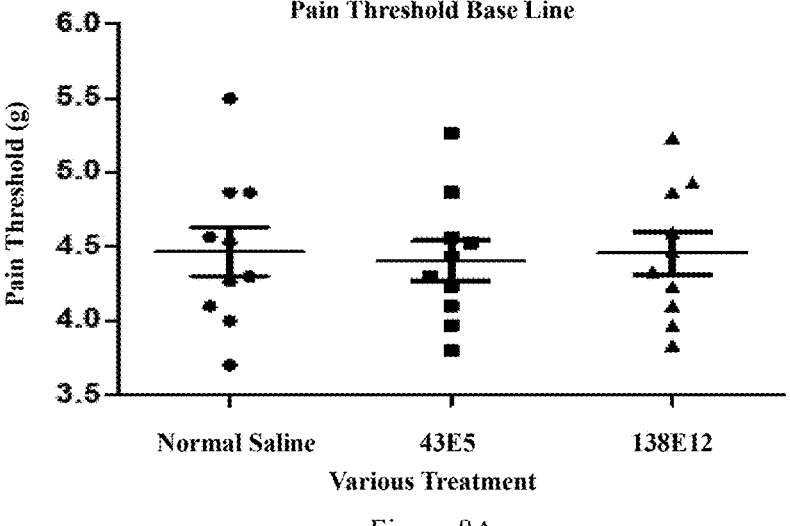

Example 9: the Effect of Anti-NGF Antibody on CFA-Induced Inflammatory Pain in Mice C57BL/6 mice (Zhejiang Weitong Lihua Laboratory Animal Technology Co., Ltd.), male, SPF grade, 6-8 weeks old, were kept for 5-day adaptive feeding. After the adaptation period, the animals were divided into 3 groups, namely the normal saline group, the anti-NGF antibody 43E5 group, and the anti-NGF antibody 138E12 group, with 10 animals in each group. Before the injection of the modeling agent CFA into the planta of mice, VonFrey was used to measure the pain threshold for 3 times (with an interval of no less than 10 minutes), and the average value of the 3 measurements was taken as the basal pain threshold (FIG. 8A).

On the next day, mice were injected with 25 µl of CFA into the planta of the left hind foot to induce inflammation (the ratio of CFA and liquid paraffin was 1:1). After the toes were significantly swollen (about 24 hours after modeling), the pain threshold of the left hind foot of the mouse was detected for 3 times in the same way, and the average value was taken as the pain threshold of pre-administration (FIG. 8B).

Figure 8E:
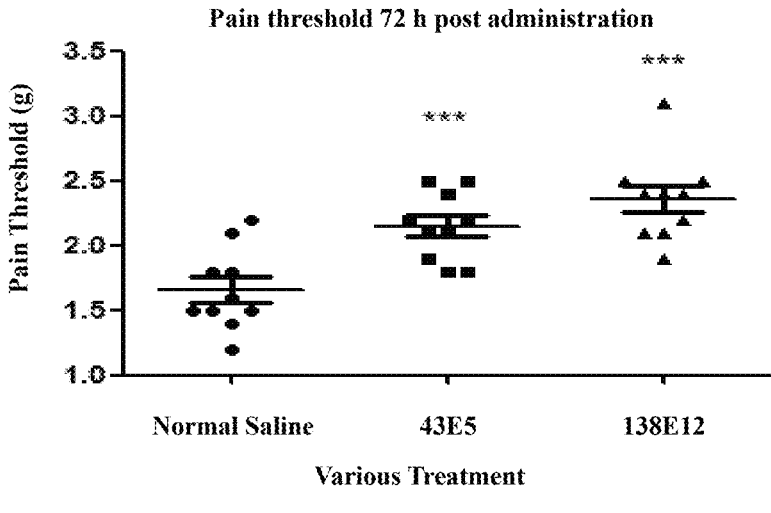

Subsequently, each group were subcutaneously injected with normal saline, anti-NGF antibody 43E5, and anti-NGF antibody 138E12 at a dose of 10 mg/kg, and the pain threshold was measured once at 24 hours, 48 hours, and 72 hours post administration (FIGS. 8C-8E). The effects of the test substances on pain threshold were evaluated.

The results are shown in FIGS. 8A-8E. Both anti-NGF antibody 43E5 and 138E12 can significantly improve the decrease of the pain threshold induced by CFA at 24 h, 48 h and 72 h post administration, and there are statistical differences compared to the normal saline group.

Example 10: Humanization and Characterization of Murine Anti-NGF Antibody

A. Humanization of Antibodies

Humanization was carried out according to the light chain variable region (VL) and heavy chain variable region (VH) sequences of the antibodies secreted by the hybridoma cells obtained above. The amino acid sequences of murine antibody VL and VH were aligned and searched in the human embryonic antibody amino acid sequence database, to find human IGHV and IGKV sequences with high homology as humanization templates. The potential steric hindrance and interaction between the amino acids of the variable region and the framework region are analyzed by computer simulation technology, to determine the amino acids in the framework region that are critical for maintaining the activity of the humanized antibody. Such amino acids were retained during the humanization process. Humanization of the light and heavy chain variable regions was accomplished by CDR grafting technology. Then, the following humanized antibodies were obtained with the selected antibody constant region templates. Anti-NGF antibody 43E5 uses human IGHV1-2 as the heavy chain variable region template and human IGKV2-30 as the light chain variable region template, to obtain antibodies 43E5-01 and 43E5-02. Human IGHV1-69 was used as the heavy chain variable region template and human IGKV2-30 was used as the light chain variable region template to obtain antibodies 43E5-05 and 43E5-06. The four antibodies 43E5-01, 43E5-02, 43E5-05 and 43E5-06 share the same light chain variable region sequence. Anti-NGF antibody 138E12 uses human IGHV4-59 as the heavy chain variable region template and human IGKV1-39 as the light chain variable region template, to obtain antibodies 138E12-01 and 138E12-02. The antibodies 138E12-01 and 138E12-02 have the same amino acid sequence of the light chain variable region, and different amino acid sequence of the heavy chain variable region. In addition, since antibodies 138E12-01 and 138E12-02 comprise isomerization site DG and deamidation site NS in the heavy chain complementarity determining region sequence, the heavy chain variable regions of these antibodies were further engineered in order to remove the potential impact of the above sites on the antibodies. 138E12-01 was used as a template, and in VH, $DG_{54\text{-}55}$ was mutated to $EG_{54\text{-}55}$, $NS_{60\text{-}61}$ was mutated to $QS_{60\text{-}61}$, or $DG_{54\text{-}55}$ was mutated to EG$_{54-55}$ and NS$_{60-61}$ was mutated to QS$_{60-61}$, thereby resulting in the antibodies 138E12-08, 138E12-09 and 138E12-10, respectively. 138E12-02 was used as a template, and in VH, DG$_{54-55}$ was mutated to EG$_{54-55}$, DG$_{54-55}$ was mutated to DA$_{54-55}$, NS$_{60-61}$ was mutated to QS$_{60-61}$, NS$_{60-61}$ was mutated to NT$_{60-61}$, or DG$_{54-55}$ was mutated to EG$_{54-55}$ and NS$_{60-61}$ was mutated to QS$_{60-61}$, thereby resulting in antibodies 138E12-03, 138E12-04, 138E12-05, 138E12-06 and 138E12-11. 138E12-07 was obtained by using human IGHV4-59 as the heavy chain variable region and human IGKV1-39 as the light chain variable region, where the framework region sequence of the heavy chain variable region was fully derived from human, without murine amino acids, however, in its heavy chain complementarity determining region, DG$_{54-55}$ was mutated to EG$_{54-55}$ and NS$_{60-61}$ was mutated to QS$_{60-61}$.

The humanized antibody heavy chain and light chain were separately genetically synthesized, and then ligated into the corresponding plasmid after enzyme digestion. The constructed plasmid was transiently transfected into CHO cells for expression. After 7-10 days of expression, the cell culture supernatant was purified using Mab Select column (GE Healthcare) equilibrated with a corresponding buffer (such as phosphate buffered saline (pH 7.4)), and then eluted with sodium citrate or other buffers. The resulting antibodies can be identified by SDS-PAGE or SEC-HPLC for purity and other subsequent characterization studies.

The variable region amino acid sequences of the antibodies described above are shown in Table 9:

TABLE 9

| Humanized antibody variable region sequences of anti-NGF antibodies 43E5, 138E12 | | | | |
|---|---|---|---|---|
| | Heavy chain | | Light chain | |
| Antibody number | Amino acid sequence of the heavy chain: | Nucleic acid sequence of the heavy drain: | Amino acid sequence of the light drain: | Nucleic acid sequence of the light drain: |
| 43E5-01 | SEQ ID NO: 33 | SEQ ID NO: 34 | SEQ ID NO: 31 | SEQ ID NO: 32 |
| 43E5-02 | SEQ ID NO: 35 | SEQ ID NO: 36 | | |
| 43E5-05 | SEQ ID NO: 37 | SEQ ID NO: 38 | | |
| 43E5-06 | SEQ ID NO: 39 | SEQ ID NO: 40 | | |
| 138E12-01 | SEQ ID NO: 43 | SEQ ID NO: 44 | SEQ ID NO: 41 | SEQ ID NO: 42 |
| 138E12-02 | SEQ ID NO: 45 | SEQ ID NO: 46 | | |
| 138E12-03 | SEQ ID NO: 47 | SEQ ID NO: 48 | | |
| 138E12-04 | SEQ ID NO: 49 | SEQ ID NO: 50 | | |
| 138E12-05 | SEQ ID NO: 51 | SEQ ID NO: 52 | | |
| 138E12-06 | SEQ ID NO: 53 | SEQ ID NO: 54 | | |
| 138E12-07 | SEQ ID NO: 55 | SEQ ID NO: 56 | | |
| 138E12-08 | SEQ ID NO: 57 | SEQ ID NO: 58 | | |
| 138E12-09 | SEQ ID NO: 59 | SEQ ID NO: 60 | | |
| 138E12-10 | SEQ ID NO: 61 | SEQ ID NO: 62 | | |
| 138E12-11 | SEQ ID NO: 63 | SEQ ID NO: 64 | | |

Humanized Antibody Variable Region Sequences of Anti-NGF Antibody 43E5

The humanized antibodies 43E5-01, 43E5-02, 43E5-05 and 43E5-06 from anti-NGF antibody 43E5 comprise the same light chain.

Amino acid sequence of the light chain variable region:

(SEQ ID NO: 31)
DVVMTQSPLSLPVTLGQPASISCKSSQSLLHSVGKTYLNWLQQRPGQSPR

RLIYLVSKLDSGVPDRFSGSGSGTDFTLKISRVEAEDVGVYFCWQGTHLP

QTFGGGTKVEIK

Nucleic acid sequence of the light chain variable region:

(SEQ ID NO: 32)
GACGTGGTCATGACACAGAGCCCACTGTCTCTGCCTGTGACCCTGGGACA

GCCAGCCTCTATCTCCTGCAAGTCCAGCCAGTCCCTGCTGCACAGCGTGG

GCAAGACATACCTGAACTGGCTGCAGCAGAGGCCAGGACAGAGCCCAAGG

CGGCTGATCTATCTGGTGTCTAAGCTGGACTCCGGCGTGCCTGATAGATT

CAGCGGCTCTGGCTCCGGCACCGACTTTACACTGAAGATCTCTCGCGTGG

AGGCTGAGGATGTGGGCGTGTACTTCTGTTGGCAGGGCACCCATCTGCCA

CAGACATTTGGCGGCGGCACCAAGGTGGAGATCAAG

43E5-01:
Amino acid sequence of the heavy chain variable region:

(SEQ ID NO: 33)
QVQLVQSGAEVKKPGASVKVSCKASGYTFTDYEMHWVRQAPGQGLEWMGA

IDPETGGTAYNQKFKGRVTMTADKSISTAYMELSRLRSDDTAVYYCRRGA

NLNHYGNDEGSYWGQGTLVTVSS

Nucleic acid sequence of the heavy chain variable region:

(SEQ ID NO: 34)
CAGGTGCAGCTGGTGCAGTCCGGAGCTGAGGTGAAGAAGCCAGGAGCCTC

CGTGAAGGTGTCTTGCAAGGCCTCCGGCTACACCTTCACAGACTATGAGA

TGCACTGGGTGAGGCAGGCTCCAGGACAGGGACTGGAGTGGATGGGAGCT

ATCGATCCTGAGACCGGAGGAACAGCTTACAACCAGAAGTTTAAGGGCAG

AGTGACCATGACAGCCGACAAGTCTATCTCCACCGCTTATATGGAGCTGA

GCAGACTGCGCTCTGACGATACAGCCGTGTACTATTGTAGGCGGGGCGCT

AACCTGAATCATTACGGCAATGATGAGGGCTCCTATTGGGGCCAGGGCAC

CCTGGTGACAGTGTCCAGC

43E5-02:
Amino acid sequence of the heavy chain variable region:

(SEQ ID NO: 35)
QVQLVQSGAEVKKPGASVKVSCKASGYTFTDYEMHWVRQAPGQGLEWIGA

IDPETGGTAYNQKFKGRATLTADKSISTAYMELSRLRSDDTAVYYCRRGA

NLNHYGNDEGSYWGQGTLVTVSS

Nucleic acid sequence of the heavy chain variable region:

(SEQ ID NO: 36)
CAGGTGCAGCTGGTGCAGTCCGGAGCTGAGGTGAAGAAGCCAGGAGCCTC

CGTGAAGGTGTCTTGCAAGGCCTCCGGCTACACCTTCACAGACTATGAGA

TGCACTGGGTGAGGCAGGCTCCAGGACAGGGACTGGAGTGGATCGGAGCT

-continued

ATCGATCCTGAGACCGGAGGAACAGCTTACAACCAGAAGTTTAAGGGCAG

AGCCACCCTGACAGCTGACAAGTCTATCTCCACCGCCTATATGGAGCTGA

GCAGACTGCGCTCTGACGATACAGCCGTGTACTATTGTAGGCGGGGCGCT

AACCTGAATCATTACGGCAATGATGAGGGCTCCTATTGGGGCCAGGGCAC

CCTGGTGACAGTGTCCAGC

43E5-05:
Amino acid sequence of the heavy chain variable
region:
                                    (SEQ ID NO: 37)
QVQLVQSGAEVKKPGSSVKVSCKASGYTFTDYEMHWVRQAPGQGLEWMGA

IDPETGGTAYNQKFKGRVTITADKSTSTAYMELSSLRSEDTAVYYCRRGA

NLNHYGNDEGSYWGQGTLVTVSS

Nucleic acid sequence of the heavy chain variable
region:
                                    (SEQ ID NO: 38)
CAGGTGCAGCTGGTGCAGTCCGGAGCTGAGGTGAAGAAGCCAGGCTCCAG

CGTGAAGGTGTCTTGCAAGGCTTCCGGCTACACCTTCACAGACTATGAGA

TGCACTGGGTGAGGCAGGCTCCAGGACAGGGACTGGAGTGGATGGGAGCT

ATCGATCCTGAGACCGGAGGAACAGCTTACAACCAGAAGTTTAAGGGCAG

AGTGACCATCACAGCCGACAAGTCCACCAGCACAGCTTATATGGAGCTGT

CTTCCCTGCGCAGCGAGGATACCGCCGTGTACTATTGTAGGCGGGGCGCT

-continued

AACCTGAATCATTACGGCAATGACGAGGGCTCTTATTGGGGCCAGGGCAC

CCTGGTGACAGTGAGCTCT

43E5-06:
Amino acid sequence of the heavy chain variable
region:
                                    (SEQ ID NO: 39)
QVQLVQSGAEVKKPGSSVKVSCKASGYTFTDYEMHWVRQAPGQGLEWIGA

IDPETGGTAYNQKFKGRATLTADKSTSTAYMELSSLRSEDTAVYYCRRGA

NLNHYGNDEGSYWGQGTLVTVSS

Nucleic acid sequence of the heavy chain variable
region:
                                    (SEQ ID NO: 40)
CAGGTGCAGCTGGTGCAGTCCGGAGCTGAGGTGAAGAAGCCAGGCTCCAG

CGTGAAGGTGTCTTGCAAGGCTTCCGGCTACACCTTCACAGACTATGAGA

TGCACTGGGTGAGGCAGGCTCCAGGACAGGGACTGGAGTGGATCGGAGCT

ATCGATCCTGAGACCGGAGGAACAGCTTACAACCAGAAGTTTAAGGGCAG

AGCCACCCTGACAGCTGACAAGTCCACCAGCACAGCTTATATGGAGCTGT

CTTCCCTGCGCAGCGAGGATACCGCCGTGTACTATTGTAGGCGGGGCGCT

AACCTGAATCATTACGGCAATGACGAGGGCTCTTATTGGGGCCAGGGCAC

CCTGGTGACAGTGAGCTCT

Humanized Antibody Variable Region Sequences of Anti-NGF Antibody 138E12

The humanized antibodies 138E12-01, 138E12-02, 138E12-03, 138E12-04, 138E12-05, 138E12-06, 138E12-07, 138E12-08, 138E12-09, 138E12-10 and 138E12-11 of anti-NGF antibody 138E12 comprise the same light chain.

Amino acid sequence of the light chain variable region:
                                    (SEQ ID NO: 41)
DIQMTQSPSSLSASVGDRVTITCRASQDISNYLNWYQQKPGKAPKLLIYYTSRLHSGVPSRFSGSGSGTDY

TLTISSLQPEDFATYFCQQGNTLPRTFGGGTKVEIK

Nucleic acid sequence of the light chain variable region:
                                    (SEQ ID NO: 42)
GACATCCAGATGACCCAGAGCCCCAGCAGCCTGAGCGCCAGCGTGGGCGACAGAGTGACCATCACCTGCAG

AGCCAGCCAGGACATCAGCAACTACCTGAACTGGTACCAGCAGAAGCCCGGCAAGGCCCCCAAGCTGCTGA

TCTACTACACCAGCAGACTGCACAGCGGCGTGCCCAGCAGATTCAGCGGCAGCGGCAGCGGCACCGACTAC

ACCCTGACCATCAGCAGCCTGCAGCCCGAGGACTTCGCCACCTACTTCTGCCAGCAGGGCAACACCCTGCC

CAGAACCTTCGGCGGCGGCACCAAGGTGGAGATCAAG

138E12-01:
Amino acid sequence of the heavy chain variable region:
                                    (SEQ ID NO: 43)
QVQLQESGPGLVKPSETLSLTCTVSGFSLTGYGVNWIRQPPGKGLEWIGMIWFDGSTDYNSALKSRVTISK

DNSKSQVSLKLSSVTAADTAVYYCAREGYYYGTTYYFDYWGQGTTVTVSS

Nucleic acid sequence of the heavy chain variable region:
                                    (SEQ ID NO: 44)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGA

TCGGCATGATCTGGTTCGACGGCAGCACCGACTACAACAGCGCCCTGAAGAGCAGAGTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

-continued

138E12-02:
Amino acid sequence of the heavy chain variable region:

(SEQ ID NO: 45)

QVQLQESGPGLVKPSETLSLTCTVSGFSLTGYGVNWIRQPPGKGLEWLGMIWFDGSTDYNSALKSRLTISK

DNSKSQVSLKLSSVTAADTAVYYCAREGYYYGTTYYFDYWGQGTTVTVSS

Nucleic acid sequence of the heavy chain variable region:

(SEQ ID NO: 46)

CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGC

TGGGCATGATCTGGTTCGACGGCAGCACCGACTACAACAGCGCCCTGAAGAGCAGACTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

138E12-03:
Amino acid sequence of the heavy chain variable region:

(SEQ ID NO: 47)

QVQLQESGPGLVKPSETLSLTCTVSGFSLTGYGVNWIRQPPGKGLEWLGMIWFEGSTDYNSALKSRLTISK

DNSKSQVSLKLSSVTAADTAVYYCAREGYYYGTTYYFDYWGQGTTVTVSS

Nucleic acid sequence of the heavy chain variable region:

(SEQ ID NO: 48)

CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGC

TGGGCATGATCTGGTTCGAGGGCAGCACCGACTACAACAGCGCCCTGAAGAGCAGACTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

138E12-04:
Amino acid sequence of the heavy chain variable region:

(SEQ ID NO: 49)

QVQLQESGPGLVKPSETLSLTCTVSGFSLTGYGVNWIRQPPGKGLEWLGMIWFDASTDYNSALKSRLTISK

DNSKSQVSLKLSSVTAADTAVYYCAREGYYYGTTYYFDYWGQGTTVTVSS

Nucleic acid sequence of the heavy chain variable region:

(SEQ ID NO: 50)

CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGC

TGGGCATGATCTGGTTCGACGCCAGCACCGACTACAACAGCGCCCTGAAGAGCAGACTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

138E12-05:
Amino acid sequence of the heavy chain variable region:

(SEQ ID NO: 51)

QVQLQESGPGLVKPSETLSLTCTVSGFSLTGYGVNWIRQPPGKGLEWLGMIWFDGSTDYQSALKSRLTISK

DNSKSQVSLKLSSVTAADTAVYYCAREGYYYGTTYYFDYWGQGTTVTVSS

Nucleic acid sequence of the heavy chain variable region:

(SEQ ID NO: 52)

CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGC

-continued

TGGGCATGATCTGGTTCGACGGCAGCACCGACTACCAGAGCGCCCTGAAGAGCAGACTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC
138E12-06:
Amino acid sequence of the heavy chain variable region:
                                                                              (SEQ ID NO: 53)
QVQLQESGPGLVKPSETLSLTCTVSGFSLTGYGVNWIRQPPGKGLEWLGMIWFDGSTDYNTALKSRLTISK

DNSKSQVSLKLSSVTAADTAVYYCAREGYYYGTTYYFDYWGQGTTVTVSS

Nucleic acid sequence of the heavy chain variable region:
                                                                              (SEQ ID NO: 54)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGC

TGGGCATGATCTGGTTCGACGGCAGCACCGACTACAACACCGCCCTGAAGAGCAGACTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

138E12-07:
Amino acid sequence of the heavy chain variable region:
                                                                              (SEQ ID NO: 55)
QVQLQESGPGLVKPSETLSLTCTVSGFSLTGYGVNWIRQPPGKGLEWIGMIWFEGSTDYQSALKSRVTISV

DTSKNQFSLKLSSVTAADTAVYYCAREGYYYGTTYYFDYWGQGTTVTVSS

Nucleic acid sequence of the heavy chain variable region:
                                                                              (SEQ ID NO: 56)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGA

TCGGCATGATCTGGTTCGAGGGCAGCACCGACTACCAGAGCGCCCTGAAGAGCAGAGTGACCATCAGCGTG

GACACCAGCAAGAACCAGTTCAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

138E12-08:
Amino acid sequence of the heavy chain variable region:
                                                                              (SEQ ID NO: 57)
QVQLQESGPGLVKPSETLSLTCTVSGFSLTGYGVNWIRQPPGKGLEWIGMIWFEGSTDYNSALKSRVTISK

DNSKSQVSLKLSSVTAADTAVYYCAREGYYYGTTYYFDYWGQGTTVTVSS

Nucleic acid sequence of the heavy chain variable region:
                                                                              (SEQ ID NO: 58)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGA

TCGGCATGATCTGGTTCGAGGGCAGCACCGACTACAACAGCGCCCTGAAGAGCAGAGTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC

138E12-09:
Amino acid sequence of the heavy chain variable region:
                                                                              (SEQ ID NO: 59)
QVQLQESGPGLVKPSETLSLTCTVSGFSLTGYGVNWIRQPPGKGLEWIGMIWFDGSTDYQSALKSRVTISK

DNSKSQVSLKLSSVTAADTAVYYCAREGYYYGTTYYFDYWGQGTTVTVSS

-continued

Nucleic acid sequence of the heavy chain variable region:
```
                                              (SEQ ID NO: 60)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGA

TCGGCATGATCTGGTTCGACGGCAGCACCGACTACCAGAGCGCCCTGAAGAGCAGAGTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC
```

138E12-10:
Amino acid sequence of the heavy chain variable region:
```
                                              (SEQ ID NO: 61)
QVQLQESGPGLVKPSETLSLTCTVSGFSLTGYGVNWIRQPPGKGLEWIGMIWFEGSTDYQSALKSRVTISK

DNSKSQVSLKLSSVTAADTAVYYCAREGYYYGTTYYFDYWGQGTTVTVSS
```

Nucleic acid sequence of the heavy chain variable region:
```
                                              (SEQ ID NO: 62)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGA

TCGGCATGATCTGGTTCGAGGGCAGCACCGACTACCAGAGCGCCCTGAAGAGCAGAGTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC
```

138E12-11:
Amino acid sequence of the heavy chain variable region:
```
                                              (SEQ ID NO: 63)
QVQLQESGPGLVKPSETLSLTCTVSGFSLTGYGVNWIRQPPGKGLEWLGMIWFEGSTDYQSALKSRLTISK

DNSKSQVSLKLSSVTAADTAVYYCAREGYYYGTTYYFDYWGQGTTVTVSS
```

Nucleic acid sequence of the heavy chain variable region:
```
                                              (SEQ ID NO: 64)
CAGGTGCAGCTGCAGGAGAGCGGCCCCGGCCTGGTGAAGCCCAGCGAGACCCTGAGCCTGACCTGCACCGT

GAGCGGCTTCAGCCTGACCGGCTACGGCGTGAACTGGATCAGACAGCCCCCCGGCAAGGGCCTGGAGTGGC

TGGGCATGATCTGGTTCGAGGGCAGCACCGACTACCAGAGCGCCCTGAAGAGCAGACTGACCATCAGCAAG

GACAACAGCAAGAGCCAGGTGAGCCTGAAGCTGAGCAGCGTGACCGCCGCCGACACCGCCGTGTACTACTG

CGCCAGAGAGGGCTACTACTACGGCACCACCTACTACTTCGACTACTGGGGCCAGGGCACCACCGTGACCG

TGAGCAGC
```

B. Characterization of Humanized Anti-NGF Antibody 1) the Binding of Humanized Antibody to Human NGF The affinity and specificity of humanized antibody were investigated by using human NGF as an antigen (Beijing Yiqiao Shenzhou Technology Co., Ltd., 11050-HNAC). NGF was diluted with 35 coating solution (PBS), and each well of 96-well microtiter plate was coated with 50 ng, after washing and blocking, and then added with serially diluted antibodies, and incubated at room temperature for 1 hour. After washing three times, HRP-conjugated donkey anti-human IgG antibody (Biolegend) was added and reacted at room temperature for 1 hour. After washing three times, tetramethylbenzidine (TMB, Biolegend) was added for color development. 1M HC1 was 40 used to terminate the color development, and the absorbance values were read at 450 nm with a microplate reader.

Figure 9A:
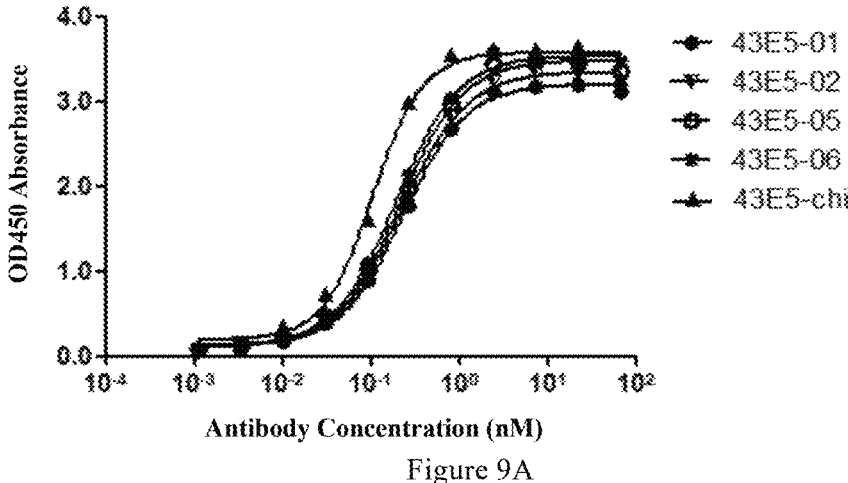
FIGS. 9A and 9B show that the humanized anti-NGF antibody of the present invention binds to human NGF.
Figure 9B:
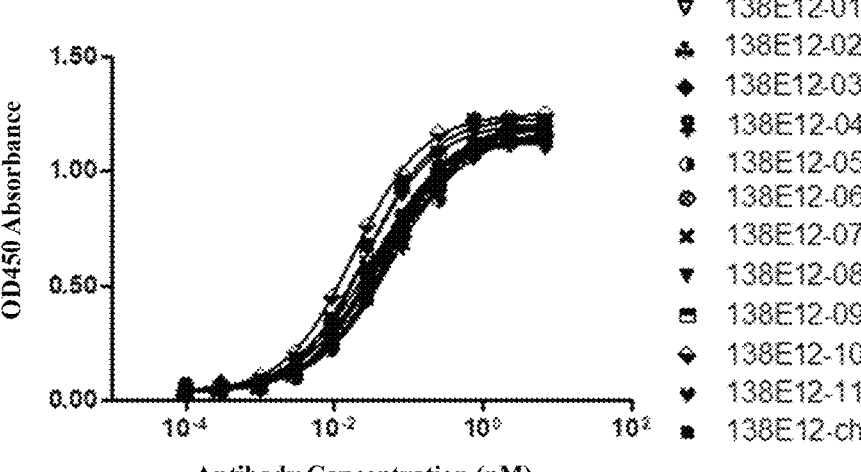

The binding results are shown in Table 10 and FIGS. 9A-9B. All the humanized antibodies of different sequences have similar binding to human NGF, and the degree of binding is comparable to that of human-mouse chimeric antibody (which contains variable regions of murine anti-NGF 45 antibody and constant regions of human antibody).

TABLE 10

| | | | Humanized anti-NGF antibody binding EC50 to human NG | | | |
|---|---|---|---|---|---|---|
| Antibody | 43E5-01 | 43E5-02 | 43E5-05 | 43E5-06 | 43E5-chi | — |
| EC50 (nM) | 0.229 | 0.222 | 0.214 | 0.192 | 0.104 | — |
| Antibody | 138E12-01 | 138E12-02 | 138E12-03 | 138E12-04 | 138E12-05 | 138E12-06 |
| EC50 (nM) | 0.0403 | 0.0420 | 0.0392 | 0.0570 | 0.0634 | 0.0500 |
| Antibody | 138E12-07 | 138E12-08 | 138E12-09 | 138E12-10 | 138E12-11 | 138E12-Chi |
| EC50 (nM) | 0.0340 | 0.0253 | 0.0270 | 0.0184 | 0.0324 | 0.0454 |

2) Humanized Antibody Binding to Other NGF Family Proteins

Figure 10A:
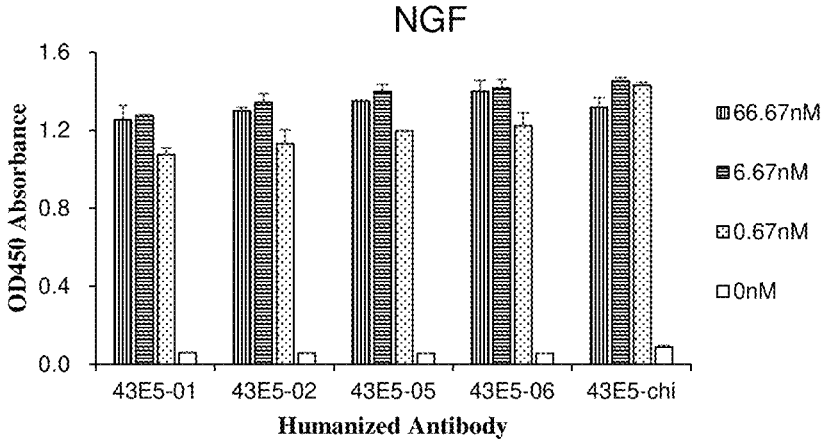
FIGS. 10A-10H show that the humanized anti-NGF antibody of the present invention binds to NGF homo-family proteins.
Figure 10B:
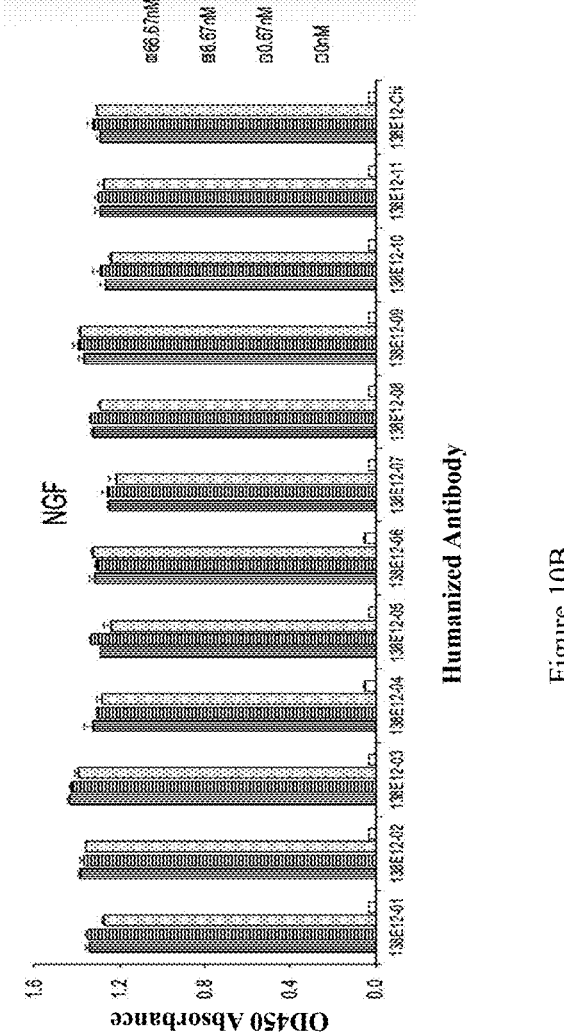
Figure 10C:
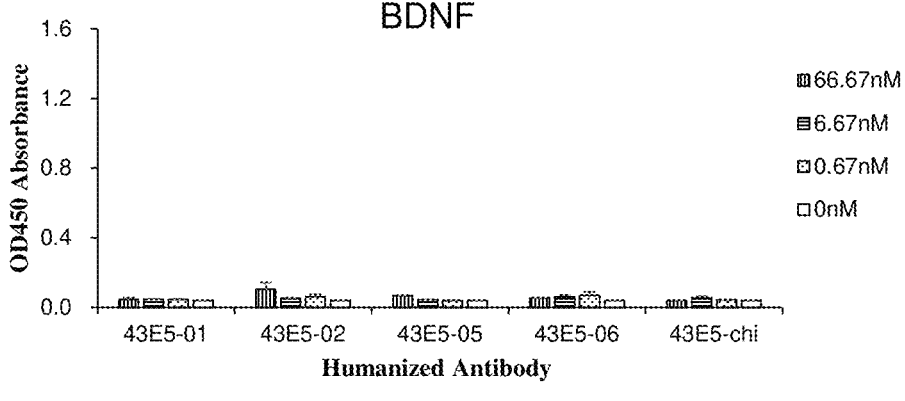
Figure 10D:
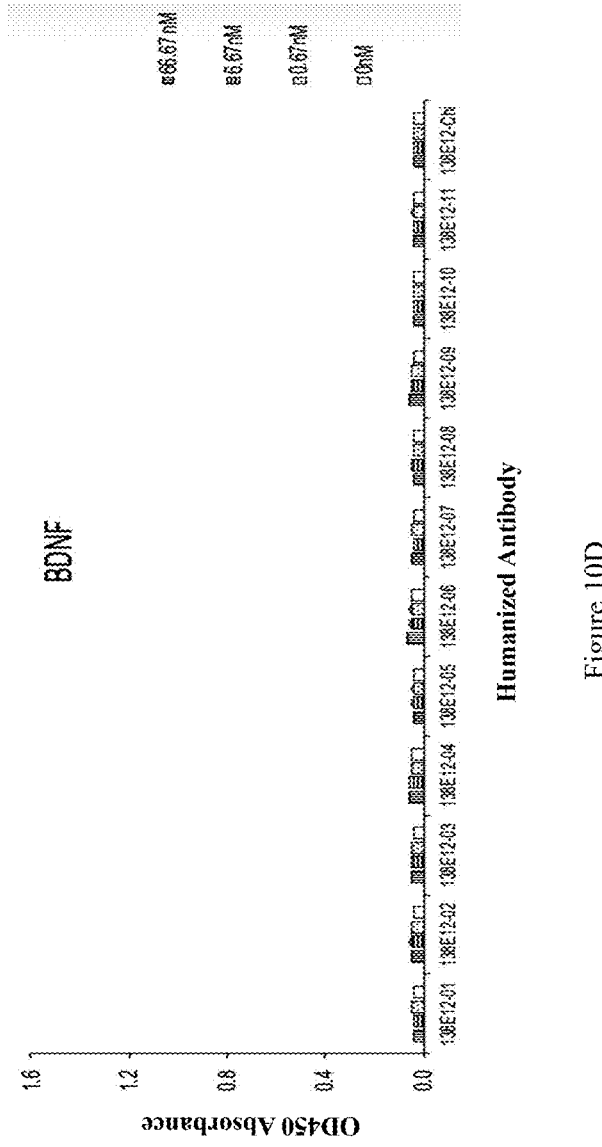
Figure 10E:
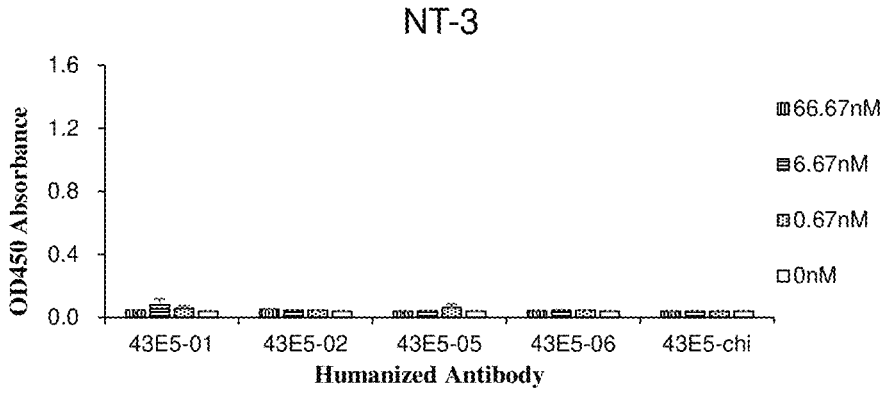
Figure 10F:
Figure 10G:
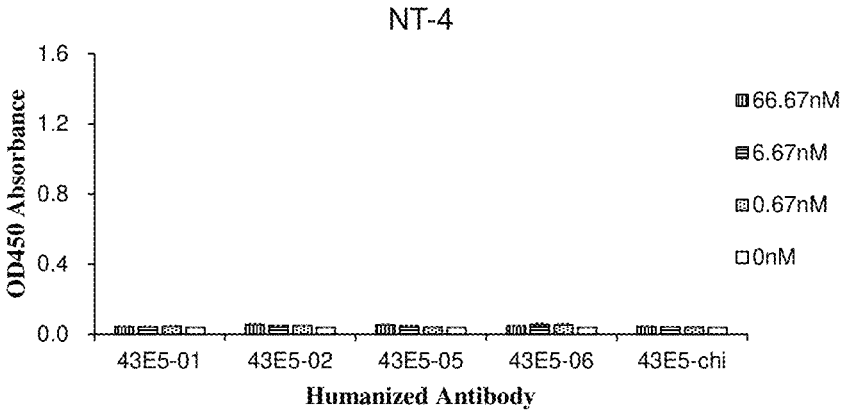
Figure 10H:
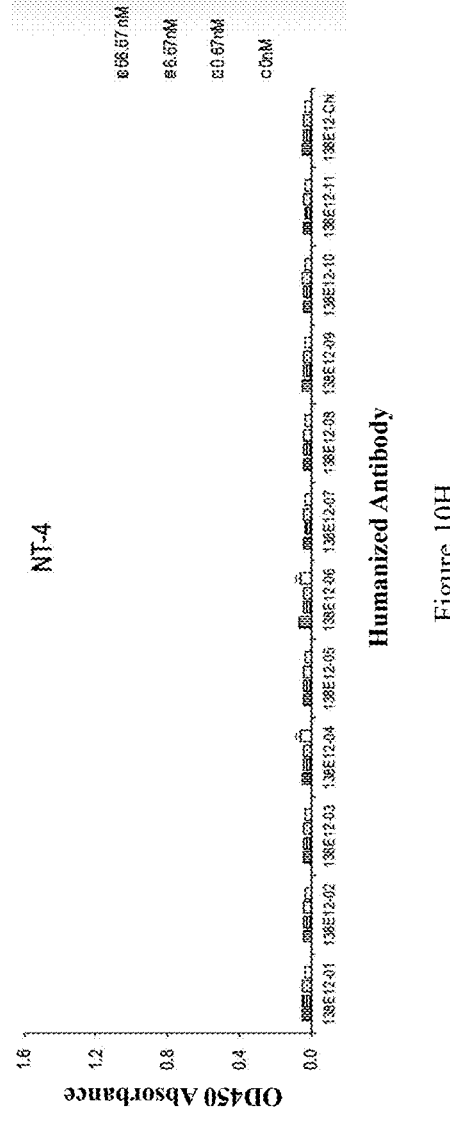
Figures 11A, 11B:
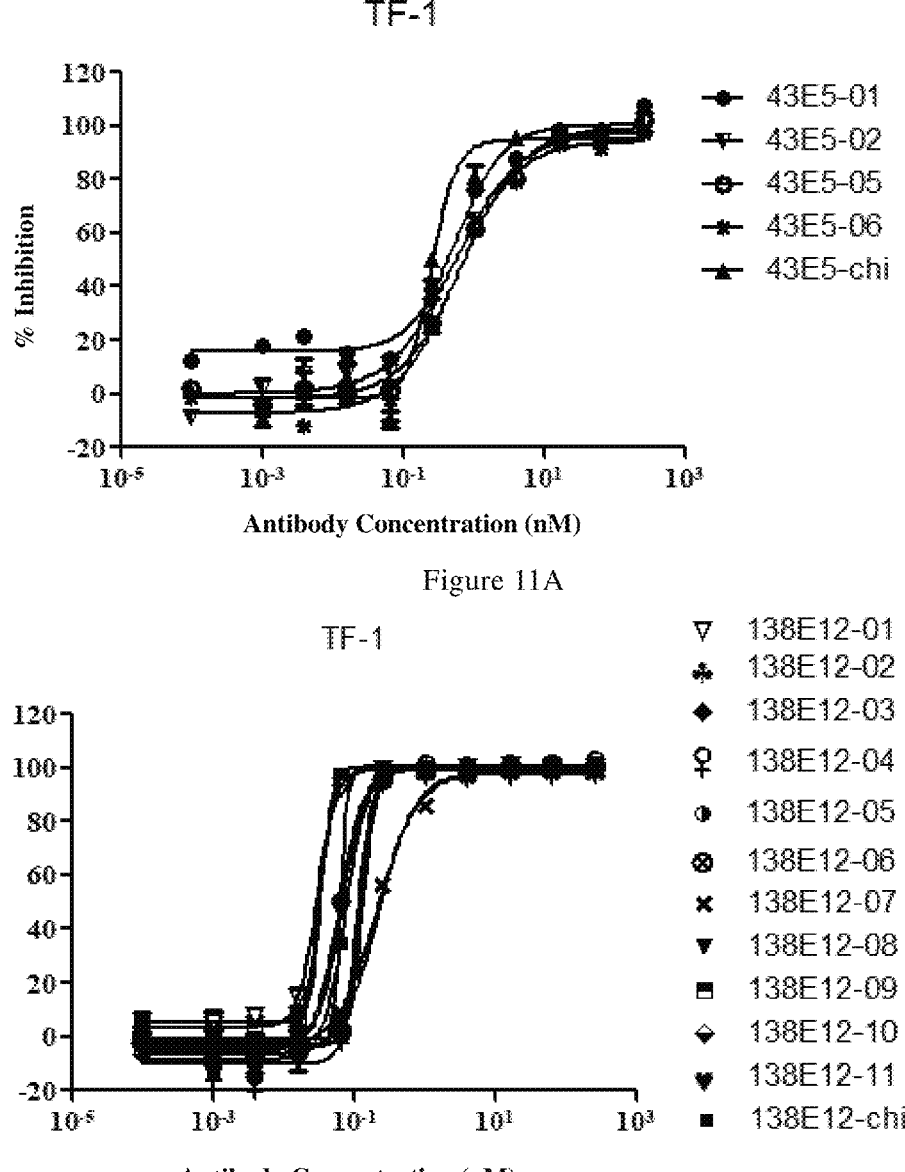
FIGS. 11A and 11B show that the humanized anti-NGF antibody of the present invention inhibits NGF-induced proliferation of TF-1 cell.

The binding of the humanized anti-NGF antibody to human NGF and to three homo-family proteins was detected according to the ELISA method described in Example 6A. The results are shown in the FIGS. 10A-10H, the humanized antibodies have high affinity to NGF (FIGS. 10A and 10B), and substantially do not bind to BDNF (FIGS. 10C and 10D), NT-3 (FIGS. 10E and 10F) or NT-4 (FIGS. 10G and 10H).

3) NGF Induced TF-1 Cell Proliferation Assay

The neutralizing activity of the humanized anti-NGF antibodies was detected by proliferation of TF-1 cells as described in Example 5A. The results are shown in re 11, all the humanized antibodies can inhibit the proliferation of TF-1 cells induced by NGF, and most of the humanized antibodies have inhibitory ability comparable to that of the human-mouse chimeric antibody. The IC50 values are shown in Table 11.

TABLE 11

| | | IC50 values of the humanized anti-NGF antibodies inhibiting NGF-induced proliferation of TF-1 cell | | | | |
|---|---|---|---|---|---|---|
| Antibody | 43E5-01 | 43E5-02 | 43E5-05 | 43E5-06 | 43E5-chi | — |
| IC50 (nM) | 0.582 | 0.534 | 0.701 | 0.568 | 0.255 | — |
| Antibody | 138E12-01 | 138E12-02 | 138E12-03 | 138E12-04 | 138E12-05 | 138E12-06 |
| IC50 (nM) | 0.030 | 0.064 | 0.130 | 0.112 | 0.136 | 0.125 |
| Antibody | 138E12-07 | 138E12-08 | 138E12-09 | 138E12-10 | 138E12-11 | 138E12-Chi |
| IC50 (nM) | 0.214 | 0.067 | 0.035 | 0.031 | 0.062 | 0.074 |

While specific embodiments of the present invention have been illustrated and described in detail, it should be appreciated that the present invention is not intended to be limited to the specific embodiments described. Various improvements, modifications and changes can be made to the present invention without departing from the spirit and scope of the invention, and these improvements, modifications and changes are all within the scope of the invention.

We claim:

1. An antibody or antigen-binding fragment thereof capable of specifically binding to nerve growth factor (NGF), wherein,
   the antibody or antigen-binding fragment thereof comprises: VH having the sequence as set forth in SEQ ID NO: 9 and VL having the sequence as set forth in SEQ ID NO: 11;
   the VH comprises: VH CDR1 as set forth in SEQ ID NO: 19, VH CDR2 as set forth in SEQ ID NO: 20 and VH CDR3 as set forth in SEQ ID NO: 21, and the VL comprises: VL CDR1 as set forth in SEQ ID NO: 28, VL CDR2 as set forth in SEQ ID NO: 29, and VL CDR3 as set forth in SEQ ID NO: 30.

2. The antibody or antigen-binding fragment thereof according to claim 1, wherein the antibody or antigen-binding fragment thereof comprises:
   (a) a heavy chain constant region (CH) of human immunoglobulin; or
   (b) a light chain constant region (CL) of human immunoglobulin.

3. The antibody or antigen-binding fragment thereof according to claim 1, wherein the antigen-binding fragment is selected from Fab, Fab', (Fab')₂, Fv, disulfide-linked Fv, scFv, and diabody; and/or,
   the antibody is murine antibody, chimeric antibody, humanized antibody, bispecific antibody or multispecific antibody.

4. The antibody or antigen-binding fragment thereof according to claim 3, wherein the humanized antibody or antigen-binding fragment thereof comprises: a heavy chain of the sequence as set forth in any one of SEQ ID NOs: 43, 45, 47, 49, 51, 53, 55, 57, 59, 61 and 63, and/or a light chain of the sequence as set forth in SEQ ID NO: 41.

5. An isolated nucleic acid molecule encoding the antibody or antigen-binding fragment thereof according to claim 1.

6. A pharmaceutical composition comprising the antibody or antigen-binding fragment thereof according to claim 1, and a pharmaceutically acceptable carrier and/or excipient.

* * * * *

```
                         SEQUENCE LISTING

<160> NUMBER OF SEQ ID NOS: 64

<210> SEQ ID NO 1
<211> LENGTH: 123
<212> TYPE: PRT
<213> ORGANISM: Artificial Sequence
<220> FEATURE:
<223> OTHER INFORMATION: Synthesized

<400> SEQUENCE: 1

Gln Val Gln Leu Gln Gln Ser Gly Ala Glu Leu Val Arg Pro Gly Ala
1               5                   10                  15
```

-continued

```
Ser Val Thr Leu Ser Cys Lys Ala Ser Gly Tyr Thr Phe Thr Asp Tyr
        20              25              30

Glu Met His Trp Val Arg Gln Thr Pro Val His Gly Leu Glu Trp Ile
        35              40              45

Gly Ala Ile Asp Pro Glu Thr Gly Gly Thr Ala Tyr Asn Gln Lys Phe
    50              55              60

Lys Gly Lys Ala Thr Leu Thr Ala Asp Lys Ser Ser Ser Thr Ala Tyr
65              70              75              80

Met Glu Leu Arg Ser Leu Thr Ser Glu Asp Ser Ala Val Tyr Tyr Cys
            85              90              95

Arg Arg Gly Ala Asn Leu Asn His Tyr Gly Asn Asp Glu Gly Ser Tyr
            100             105             110

Trp Gly Gln Gly Thr Leu Val Thr Val Ser Ala
        115             120
```

```
<210> SEQ ID NO 2
<211> LENGTH: 369
<212> TYPE: DNA
<213> ORGANISM: Artificial Sequence
<220> FEATURE:
<223> OTHER INFORMATION: Synthesized

<400> SEQUENCE: 2
caggttcaac tgcagcagtc tggggctgag ctggtgaggc ctggggcttc agtgacgctg      60
tcctgcaagg cttcgggcta cacatttact gactatgaaa tgcactgggt gaggcagaca     120
cctgtgcatg gcctggaatg gattggagct attgatcctg aaactggtgg tactgcctac     180
aatcagaagt tcaagggcaa ggccacactg actgcagaca atcctccag cacagcctac      240 atggagctcc gcagcctgac atctgaggac tctgccgtct attactgtag aagaggggca     300
aatcttaatc actatggtaa cgacgagggt tcttactggg gccaagggac tctggtcact     360
gtctctgca                                                             369
```

```
<210> SEQ ID NO 3
<211> LENGTH: 112
<212> TYPE: PRT
<213> ORGANISM: Artificial Sequence
<220> FEATURE:
<223> OTHER INFORMATION: Synthesized

<400> SEQUENCE: 3

Asp Val Val Met Thr Gln Thr Pro Leu Thr Leu Ser Val Thr Ile Gly
1               5               10              15

Gln Pro Ala Ser Ile Ser Cys Lys Ser Ser Gln Ser Leu Leu His Ser
            20              25              30

Val Gly Lys Thr Tyr Leu Asn Trp Leu Leu Gln Arg Pro Gly Gln Ser
        35              40              45

Pro Lys Arg Leu Ile Tyr Leu Val Ser Lys Leu Asp Ser Gly Val Pro
    50              55              60

Asp Arg Phe Thr Gly Ser Gly Ser Gly Thr Asp Phe Thr Leu Lys Ile
65              70              75              80

Ser Arg Val Glu Ala Glu Asp Leu Gly Val Tyr Phe Cys Trp Gln Gly
            85              90              95

Thr His Leu Pro Gln Thr Phe Gly Gly Gly Thr Lys Leu Glu Ile Lys
            100             105             110
```

```
<210> SEQ ID NO 4
```

<211> LENGTH: 336
<212> TYPE: DNA
<213> ORGANISM: Artificial Sequence
<220> FEATURE:
<223> OTHER INFORMATION: Synthesized

<400> SEQUENCE: 4
gatgttgtga tgacccagac tccactcact ttgtcggtta ccattggaca accagcctcc      60
atctcttgta agtcaagtca gagcctctta catagtgttg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattttttgct ggcaaggtac acatcttcct    300
cagacgttcg gtggaggcac caagctggaa atcaaa                                336

<210> SEQ ID NO 5
<211> LENGTH: 119
<212> TYPE: PRT
<213> ORGANISM: Artificial Sequence
<220> FEATURE:
<223> OTHER INFORMATION: Synthesized

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
                20                  25                  30

Ala Val Asn Trp Val Arg Gln Pro Pro Gly Lys Gly Leu Glu Trp Leu
            35                  40                  45

Gly Met Ile Trp Phe Asp Gly Ser Thr Asp Tyr Asn Ser Ala Leu Lys
        50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Tyr Tyr Gly Ser Ser Trp Tyr Phe Asp Val Trp Gly Ala Gly
                100                 105                 110

Thr Thr Val Thr Val Ser Ser
            115

<210> SEQ ID NO 6
<211> LENGTH: 357
<212> TYPE: DNA
<213> ORGANISM: Artificial Sequence
<220> FEATURE:
<223> OTHER INFORMATION: Synthesized

<400> SEQUENCE: 6
caggtgcagc tgaaggagtc aggacctggc ctggtggcgc cctcacagag cctgtccatc      60
acatgcaccg tctcagggtt ctcattaacc ggctatgctg taaactgggt tcgccagcct     120
ccaggaaagg gtctggagtg gctgggaatg atatggtttg atggaagcac agactataat     180
tcagctctca aatccagact gagcatcagc aaggacaact ccaagagcca gttttctta      240 aaaatgaaca gtctgcaaac tgatgacaca gccaggtact actgtgccag agactactac     300
ggtagtagct ggtacttcga tgtctggggc gcagggacca cggtcaccgt ctcctca        357

<210> SEQ ID NO 7
<211> LENGTH: 107

-continued

<212> TYPE: PRT
<213> ORGANISM: Artificial Sequence
<220> FEATURE:
<223> OTHER INFORMATION: Synthesized

<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Tyr Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Asp Ile Lys
            100                 105

<210> SEQ ID NO 8
<211> LENGTH: 321
<212> TYPE: DNA
<213> ORGANISM: Artificial Sequence
<220> FEATURE:
<223> OTHER INFORMATION: Synthesized

<400> SEQUENCE: 8
gatatccaga tgacacagac tacatcctcc ctgtctgcct ctctgggaga cagagtcacc        60
atcagttgca gggcaagtca ggacattagc tattatttaa actggtatca gcagaaacca       120
gatggaactg ttaaactcct gatctactac acatcaagat tacactcagg agtcccatca       180
aggttcagtg gcagtgggtc tggaacagat tattctctca ccattagcaa cctggagcaa       240
gaagatattg ccacttactt ttgccaacag ggtaatacgc ttcctcggac gttcggtgga       300
ggcaccaagc tggacatcaa a                                                 321

<210> SEQ ID NO 9
<211> LENGTH: 121
<212> TYPE: PRT
<213> ORGANISM: Artificial Sequence
<220> FEATURE:
<223> OTHER INFORMATION: Synthesized

<400> SEQUENCE: 9

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
                20                  25                  30

Gly Val Asn Trp Val Arg Gln Pro Pro Gly Lys Gly Leu Glu Trp Leu
            35                  40                  45

Gly Met Ile Trp Phe Asp Gly Ser Thr Asp Tyr Asn Ser Ala Leu Lys
        50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Glu Gly Tyr Tyr Tyr Gly Thr Thr Tyr Tyr Phe Asp Tyr Trp Gly

-continued

```
                 100              105              110

Gln Gly Thr Thr Leu Thr Val Ser Ser
        115              120

<210> SEQ ID NO 10
<211> LENGTH: 363
<212> TYPE: DNA
<213> ORGANISM: Artificial Sequence
<220> FEATURE:
<223> OTHER INFORMATION: Synthesized

<400> SEQUENCE: 10
caggtgcagc tgaaggagtc aggacctggc ctggtggcgc cctcacagag cctgtccatc      60
acatgcaccg tctcagggtt ctcattaacc ggctatggtg taaactgggt tcgccagcct     120
ccaggaaagg gtctggagtg gctgggaatg atatggtttg atggaagcac agactataat     180
tcagctctca aatccagact gagcatcagc aaggacaact ccaagagcca gtttttctta     240
aaaatgaaca gtctgcaaac tgatgacaca gccaggtact actgtgccag agagggttat     300
tactacggta ctacctacta ctttgactac tggggccaag gcaccactct cacagtctcc     360
tca                                                                   363

<210> SEQ ID NO 11
<211> LENGTH: 107
<212> TYPE: PRT
<213> ORGANISM: Artificial Sequence
<220> FEATURE:
<223> OTHER INFORMATION: Synthesized

<400> SEQUENCE: 11

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105

<210> SEQ ID NO 12
<211> LENGTH: 321
<212> TYPE: DNA
<213> ORGANISM: Artificial Sequence
<220> FEATURE:
<223> OTHER INFORMATION: Synthesized

<400> SEQUENCE: 12
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat acactcagg agtcccatca      180 aggttcagtg gcagtgggtc tggaacagat tattctctca ccattagcaa cctggagcaa     240
gaagatattg ccacttactt ttgccaacag ggtaatacgc ttcctcggac gttcggtgga     300
```
ggcaccaagc tggaaatcaa a                                                              321

<210> SEQ ID NO 13
<211> LENGTH: 10
<212> TYPE: PRT
<213> ORGANISM: Artificial Sequence
<220> FEATURE:
<223> OTHER INFORMATION: Synthesized

<400> SEQUENCE: 13

Gly Tyr Thr Phe Thr Asp Tyr Glu Met His
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthesized

<400> SEQUENCE: 14

Ala Ile Asp Pro Glu Thr Gly Gly Thr Ala Tyr Asn Gln Lys Phe Lys
1               5                   10                  15

Gly

<210> SEQ ID NO 15
<211> LENGTH: 16
<212> TYPE: PRT
<213> ORGANISM: Artificial Sequence
<220> FEATURE:
<223> OTHER INFORMATION: Synthesized

<400> SEQUENCE: 15

Arg Arg Gly Ala Asn Leu Asn His Tyr Gly Asn Asp Glu Gly Ser Tyr
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Synthesized

<400> SEQUENCE: 16

Gly Phe Ser Leu Thr Gly Tyr Ala Val Asn
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthesized

<400> SEQUENCE: 17

Met Ile Trp Phe Asp Gly Ser Thr Asp Tyr Asn Ser Ala Leu Lys Ser
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Synthesized

<400> SEQUENCE: 18

```
Ala Arg Asp Tyr Tyr Gly Ser Ser Trp Tyr Phe Asp Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthesized

<400> SEQUENCE: 19

Gly Phe Ser Leu Thr Gly Tyr Gly Val Asn
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Synthesized

<400> SEQUENCE: 20

Met Ile Trp Phe Asp Gly Ser Thr Asp Tyr Asn Ser Ala Leu Lys Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthesized

<400> SEQUENCE: 21

Ala Arg Glu Gly Tyr Tyr Tyr Gly Thr Thr Tyr Tyr Phe Asp Tyr
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthesized

<400> SEQUENCE: 22

Lys Ser Ser Gln Ser Leu Leu His Ser Val Gly Lys Thr Tyr Leu Asn
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Synthesized

<400> SEQUENCE: 23

Leu Val Ser Lys Leu Asp Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthesized

<400> SEQUENCE: 24
```

```
Trp Gln Gly Thr His Leu Pro Gln Thr
1               5

<210> SEQ ID NO 25
<211> LENGTH: 11
<212> TYPE: PRT
<213> ORGANISM: Artificial Sequence
<220> FEATURE:
<223> OTHER INFORMATION: Synthesized

<400> SEQUENCE: 25

Arg Ala Ser Gln Asp Ile Ser Tyr Tyr Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthesized

<400> SEQUENCE: 26

Tyr Thr Ser Arg Leu His Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Synthesized

<400> SEQUENCE: 27

Gln Gln Gly Asn Thr Leu Pro Arg Thr
1               5

<210> SEQ ID NO 28
<211> LENGTH: 11
<212> TYPE: PRT
<213> ORGANISM: Artificial Sequence
<220> FEATURE:
<223> OTHER INFORMATION: Synthesized

<400> SEQUENCE: 28

Arg Ala Ser Gln Asp Ile Ser Asn Tyr Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthesized

<400> SEQUENCE: 29

Tyr Thr Ser Arg Leu His Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthesized

<400> SEQUENCE: 30

Gln Gln Gly Asn Thr Leu Pro Arg Thr
```

1                5

<210> SEQ ID NO 31
<211> LENGTH: 112
<212> TYPE: PRT
<213> ORGANISM: Artificial Sequence
<220> FEATURE:
<223> OTHER INFORMATION: Synthesized

<400> SEQUENCE: 31

Asp Val Val Met Thr Gln Ser Pro Leu Ser Leu Pro Val Thr Leu Gly
1                5                10                15

Gln Pro Ala Ser Ile Ser Cys Lys Ser Ser Gln Ser Leu Leu His Ser
            20                25                30

Val Gly Lys Thr Tyr Leu Asn Trp Leu Gln Gln Arg Pro Gly Gln Ser
        35                40                45

Pro Arg Arg Leu Ile Tyr Leu Val Ser Lys Leu Asp Ser Gly Val Pro
    50                55                60

Asp Arg Phe Ser Gly Ser Gly Ser Gly Thr Asp Phe Thr Leu Lys Ile
65                70                75                80

Ser Arg Val Glu Ala Glu Asp Val Gly Val Tyr Phe Cys Trp Gln Gly
                85                90                95

Thr His Leu Pro Gln Thr Phe Gly Gly Gly Thr Lys Val Glu Ile Lys
            100                105                110

<210> SEQ ID NO 32
<211> LENGTH: 336
<212> TYPE: DNA
<213> ORGANISM: Artificial Sequence
<220> FEATURE:
<223> OTHER INFORMATION: Synthesized

<400> SEQUENCE: 32
gacgtggtca tgacacagag cccactgtct ctgcctgtga ccctgggaca gccagcctct        60
atctcctgca agtccagcca gtccctgctg cacagcgtgg caagacata cctgaactgg        120 ctgcagcaga ggccaggaca gagcccaagg cggctgatct atctggtgtc taagctggac        180
tccggcgtgc ctgatagatt cagcggctct ggctccggca ccgactttac actgaagatc        240
tctcgcgtgg aggctgagga tgtgggcgtg tacttctgtt ggcagggcac ccatctgcca        300
cagacatttg gcggcggcac caaggtggag atcaag        336

<210> SEQ ID NO 33
<211> LENGTH: 123
<212> TYPE: PRT
<213> ORGANISM: Artificial Sequence
<220> FEATURE:
<223> OTHER INFORMATION: Synthesized

<400> SEQUENCE: 33

Gln Val Gln Leu Val Gln Ser Gly Ala Glu Val Lys Lys Pro Gly Ala
1                5                10                15

Ser Val Lys Val Ser Cys Lys Ala Ser Gly Tyr Thr Phe Thr Asp Tyr
            20                25                30

Glu Met His Trp Val Arg Gln Ala Pro Gly Gln Gly Leu Glu Trp Met
        35                40                45

Gly Ala Ile Asp Pro Glu Thr Gly Gly Thr Ala Tyr Asn Gln Lys Phe
    50                55                60

Lys Gly Arg Val Thr Met Thr Ala Asp Lys Ser Ile Ser Thr Ala Tyr
65                70                75                80

```
Met Glu Leu Ser Arg Leu Arg Ser Asp Asp Thr Ala Val Tyr Tyr Cys
                85                  90                  95

Arg Arg Gly Ala Asn Leu Asn His Tyr Gly Asn Asp Glu Gly Ser Tyr
            100                 105                 110

Trp Gly Gln Gly Thr Leu Val Thr Val Ser Ser
        115                 120
```

<210> SEQ ID NO 34
<211> LENGTH: 369
<212> TYPE: DNA
<213> ORGANISM: Artificial Sequence
<220> FEATURE:
<223> OTHER INFORMATION: Synthesized

<400> SEQUENCE: 34

```
caggtgcagc tggtgcagtc cggagctgag gtgaagaagc caggagcctc cgtgaaggtg      60
tcttgcaagg cctccggcta caccttcaca gactatgaga tgcactgggt gaggcaggct     120
ccaggacagg gactggagtg gatgggagct atcgatcctg agaccggagg aacagcttac     180
aaccagaagt ttaagggcag agtgaccatg acagccgaca gtctatctc caccgcttat      240 atggagctga gcagactgcg ctctgacgat acagccgtgt actattgtag gcggggcgct     300
aacctgaatc attacggcaa tgatgagggc tcctattggg gccagggcac cctggtgaca     360
gtgtccagc                                                            369
```

<210> SEQ ID NO 35
<211> LENGTH: 123
<212> TYPE: PRT
<213> ORGANISM: Artificial Sequence
<220> FEATURE:
<223> OTHER INFORMATION: Synthesized

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Arg Ala Thr Leu Thr Ala Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Arg Arg Gly Ala Asn Leu Asn His Tyr Gly Asn Asp Glu Gly Ser Tyr
            100                 105                 110

Trp Gly Gln Gly Thr Leu Val Thr Val Ser Ser
        115                 120
```

<210> SEQ ID NO 36
<211> LENGTH: 369
<212> TYPE: DNA
<213> ORGANISM: Artificial Sequence
<220> FEATURE:
<223> OTHER INFORMATION: Synthesized

<400> SEQUENCE: 36

```
caggtgcagc tggtgcagtc cggagctgag gtgaagaagc caggagcctc cgtgaaggtg      60
```

-continued

```
tcttgcaagg cctccggcta caccttcaca gactatgaga tgcactgggt gaggcaggct     120
ccaggacagg gactggagtg gatcggagct atcgatcctg agaccggagg aacagcttac     180
aaccagaagt ttaagggcag agccaccctg acagctgaca agtctatctc caccgcctat     240
atggagctga gcagactgcg ctctgacgat acagccgtgt actattgtag gcggggcgct     300
aacctgaatc attacggcaa tgatgagggc tcctattggg gccagggcac cctggtgaca     360
gtgtccagc                                                            369
```

<210> SEQ ID NO 37
<211> LENGTH: 123
<212> TYPE: PRT
<213> ORGANISM: Artificial Sequence
<220> FEATURE:
<223> OTHER INFORMATION: Synthesized

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Ile Asp Pro Glu Thr Gly Gly Thr Ala Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Arg Arg Gly Ala Asn Leu Asn His Tyr Gly Asn Asp Glu Gly Ser Tyr
            100                 105                 110

Trp Gly Gln Gly Thr Leu Val Thr Val Ser Ser
        115                 120
```

<210> SEQ ID NO 38
<211> LENGTH: 369
<212> TYPE: DNA
<213> ORGANISM: Artificial Sequence
<220> FEATURE:
<223> OTHER INFORMATION: Synthesized

<400> SEQUENCE: 38

```
caggtgcagc tggtgcagtc cggagctgag gtgaagaagc caggctccag cgtgaaggtg      60
tcttgcaagg cttccggcta caccttcaca gactatgaga tgcactgggt gaggcaggct     120
ccaggacagg gactggagtg gatgggagct atcgatcctg agaccggagg aacagcttac     180
aaccagaagt ttaagggcag agtgaccatc acagccgaca agtccaccag cacagcttat     240
atggagctgt cttccctgcg cagcgaggat accgccgtgt actattgtag gcggggcgct     300
aacctgaatc attacggcaa tgacgagggc tcttattggg gccagggcac cctggtgaca     360
gtgagctct                                                            369
```

<210> SEQ ID NO 39
<211> LENGTH: 123
<212> TYPE: PRT
<213> ORGANISM: Artificial Sequence
<220> FEATURE:
<223> OTHER INFORMATION: Synthesized

```
<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Arg Arg Gly Ala Asn Leu Asn His Tyr Gly Asn Asp Glu Gly Ser Tyr
            100                 105                 110

Trp Gly Gln Gly Thr Leu Val Thr Val Ser Ser
        115                 120

<210> SEQ ID NO 40
<211> LENGTH: 369
<212> TYPE: DNA
<213> ORGANISM: Artificial Sequence
<220> FEATURE:
<223> OTHER INFORMATION: Synthesized

<400> SEQUENCE: 40
caggtgcagc tggtgcagtc cggagctgag gtgaagaagc caggctccag cgtgaaggtg      60
tcttgcaagg cttccggcta caccttcaca gactatgaga tgcactgggt gaggcaggct     120
ccaggacagg gactggagtg gatcggagct atcgatcctg agaccggagg aacagcttac     180
aaccagaagt ttaagggcag agccaccctg acagctgaca gtccaccag cacagcttat      240 atggagctgt cttccctgcg cagcgaggat accgccgtgt actattgtag gcggggcgct     300
aacctgaatc attacggcaa tgacgagggc tcttattggg gccagggcac cctggtgaca     360
gtgagctct                                                             369

<210> SEQ ID NO 41
<211> LENGTH: 107
<212> TYPE: PRT
<213> ORGANISM: Artificial Sequence
<220> FEATURE:
<223> OTHER INFORMATION: Synthesized

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Arg
                85                  90                  95

Thr Phe Gly Gly Gly Thr Lys Val Glu Ile Lys
```

```
                100               105

<210> SEQ ID NO 42
<211> LENGTH: 321
<212> TYPE: DNA
<213> ORGANISM: Artificial Sequence
<220> FEATURE:
<223> OTHER INFORMATION: Synthesized

<400> SEQUENCE: 42
gacatccaga tgacccagag ccccagcagc ctgagcgcca gcgtgggcga cagagtgacc      60
atcacctgca gagccagcca ggacatcagc aactacctga actggtacca gcagaagccc     120
ggcaaggccc ccaagctgct gatctactac accagcagac tgcacagcgg cgtgcccagc     180
agattcagcg gcagcggcag cggcaccgac tacaccctga ccatcagcag cctgcagccc     240
gaggacttcg ccacctactt ctgccagcag ggcaacaccc tgcccagaac cttcggcggc     300
ggcaccaagg tggagatcaa g                                               321

<210> SEQ ID NO 43
<211> LENGTH: 121
<212> TYPE: PRT
<213> ORGANISM: Artificial Sequence
<220> FEATURE:
<223> OTHER INFORMATION: Synthesized

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Phe Asp Gly Ser Thr Asp Tyr Asn Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120

<210> SEQ ID NO 44
<211> LENGTH: 363
<212> TYPE: DNA
<213> ORGANISM: Artificial Sequence
<220> FEATURE:
<223> OTHER INFORMATION: Synthesized

<400> SEQUENCE: 44
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gatcggcatg atctggttcg acggcagcac cgactacaac     180
agcgccctga agagcagagt gaccatcagc aaggacaaca gcaagagcca ggtgagcctg     240
aagctgagca gcgtgaccgc cgccgacacc gccgtgtact actgcgccag agagggctac     300
tactacggca ccacctacta cttcgactac tggggccagg gcaccaccgt gaccgtgagc     360
```

-continued

```
agc                                                                  363

<210> SEQ ID NO 45
<211> LENGTH: 121
<212> TYPE: PRT
<213> ORGANISM: Artificial Sequence
<220> FEATURE:
<223> OTHER INFORMATION: Synthesized

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Leu
        35                  40                  45

Gly Met Ile Trp Phe Asp Gly Ser Thr Asp Tyr Asn Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120

<210> SEQ ID NO 46
<211> LENGTH: 363
<212> TYPE: DNA
<213> ORGANISM: Artificial Sequence
<220> FEATURE:
<223> OTHER INFORMATION: Synthesized

<400> SEQUENCE: 46
caggtgcagc tgcaggagag cggccccggc ctggtgaagc ccagcgagac cctgagcctg    60
acctgcaccg tgagcggctt cagcctgacc ggctacggcg tgaactggat cagacagccc   120
cccggcaagg gcctggagtg gctgggcatg atctggttcg acggcagcac cgactacaac   180
agcgccctga gagcagact gaccatcagc aaggacaaca gcaagagcca ggtgagcctg    240
aagctgagca gcgtgaccgc cgccgacacc gccgtgtact actgcgccag agagggctac    300
tactacggca ccacctacta cttcgactac tggggccagg gcaccaccgt gaccgtgagc    360
agc                                                                  363

<210> SEQ ID NO 47
<211> LENGTH: 121
<212> TYPE: PRT
<213> ORGANISM: Artificial Sequence
<220> FEATURE:
<223> OTHER INFORMATION: Synthesized

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Leu
        35                  40                  45
```

-continued

```
Gly Met Ile Trp Phe Glu Gly Ser Thr Asp Tyr Asn Ser Ala Leu Lys
    50              55              60

Ser Arg Leu Thr Ile Ser Lys Asp Asn Ser Lys Ser Gln Val Ser Leu
65              70              75              80

Lys Leu Ser Ser Val Thr Ala Ala Asp Thr Ala Val Tyr Tyr Cys Ala
                85              90              95

Arg Glu Gly Tyr Tyr Tyr Gly Thr Thr Tyr Tyr Phe Asp Tyr Trp Gly
            100             105             110

Gln Gly Thr Thr Val Thr Val Ser Ser
        115             120
```

```
<210> SEQ ID NO 48
<211> LENGTH: 363
<212> TYPE: DNA
<213> ORGANISM: Artificial Sequence
<220> FEATURE:
<223> OTHER INFORMATION: Synthesized

<400> SEQUENCE: 48
caggtgcagc tgcaggagag cggccccggc ctggtgaagc ccagcgagac cctgagcctg        60
acctgcaccg tgagcggctt cagcctgacc ggctacggcg tgaactggat cagacagccc       120
cccggcaagg gcctggagtg gctgggcatg atctggttcg agggcagcac cgactacaac       180
agcgccctga gagcagact gaccatcagc aaggacaaca gcaagagcca ggtgagcctg         240
aagctgagca gcgtgaccgc cgccgacacc gccgtgtact actgcgccag agagggctac        300
tactacggca ccacctacta cttcgactac tggggccagg gcaccaccgt gaccgtgagc        360
agc                                                                      363
```

```
<210> SEQ ID NO 49
<211> LENGTH: 121
<212> TYPE: PRT
<213> ORGANISM: Artificial Sequence
<220> FEATURE:
<223> OTHER INFORMATION: Synthesized

<400> SEQUENCE: 49
```

```
Gln Val Gln Leu Gln Glu Ser Gly Pro Gly Leu Val Lys Pro Ser Glu
1               5               10              15

Thr Leu Ser Leu Thr Cys Thr Val Ser Gly Phe Ser Leu Thr Gly Tyr
            20              25              30

Gly Val Asn Trp Ile Arg Gln Pro Pro Gly Lys Gly Leu Glu Trp Leu
        35              40              45

Gly Met Ile Trp Phe Asp Ala Ser Thr Asp Tyr Asn Ser Ala Leu Lys
    50              55              60

Ser Arg Leu Thr Ile Ser Lys Asp Asn Ser Lys Ser Gln Val Ser Leu
65              70              75              80

Lys Leu Ser Ser Val Thr Ala Ala Asp Thr Ala Val Tyr Tyr Cys Ala
                85              90              95

Arg Glu Gly Tyr Tyr Tyr Gly Thr Thr Tyr Tyr Phe Asp Tyr Trp Gly
            100             105             110

Gln Gly Thr Thr Val Thr Val Ser Ser
        115             120
```

```
<210> SEQ ID NO 50
<211> LENGTH: 363
<212> TYPE: DNA
<213> ORGANISM: Artificial Sequence
```

```
<220> FEATURE:
<223> OTHER INFORMATION: Synthesized

<400> SEQUENCE: 50
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gctgggcatg atctggttcg acgccagcac cgactacaac     180
agcgccctga gagcagact gaccatcagc aaggacaaca gcaagagcca ggtgagcctg      240
aagctgagca gcgtgaccgc cgccgacacc gccgtgtact actgcgccag agagggctac     300
tactacggca ccacctacta cttcgactac tggggccagg gcaccaccgt gaccgtgagc     360
agc                                                                   363

<210> SEQ ID NO 51
<211> LENGTH: 121
<212> TYPE: PRT
<213> ORGANISM: Artificial Sequence
<220> FEATURE:
<223> OTHER INFORMATION: Synthesized

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Leu
        35                  40                  45

Gly Met Ile Trp Phe Asp Gly Ser Thr Asp Tyr Gln Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120

<210> SEQ ID NO 52
<211> LENGTH: 363
<212> TYPE: DNA
<213> ORGANISM: Artificial Sequence
<220> FEATURE:
<223> OTHER INFORMATION: Synthesized

<400> SEQUENCE: 52
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gctgggcatg atctggttcg acggcagcac cgactaccag     180
agcgccctga gagcagact gaccatcagc aaggacaaca gcaagagcca ggtgagcctg      240
aagctgagca gcgtgaccgc cgccgacacc gccgtgtact actgcgccag agagggctac     300
tactacggca ccacctacta cttcgactac tggggccagg gcaccaccgt gaccgtgagc     360
agc                                                                   363

<210> SEQ ID NO 53
```

```
<211> LENGTH: 121
<212> TYPE: PRT
<213> ORGANISM: Artificial Sequence
<220> FEATURE:
<223> OTHER INFORMATION: Synthesized

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Leu
        35                  40                  45

Gly Met Ile Trp Phe Asp Gly Ser Thr Asp Tyr Asn Thr Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120

<210> SEQ ID NO 54
<211> LENGTH: 363
<212> TYPE: DNA
<213> ORGANISM: Artificial Sequence
<220> FEATURE:
<223> OTHER INFORMATION: Synthesized

<400> SEQUENCE: 54
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gctgggcatg atctggttcg acggcagcac cgactacaac     180
accgccctga gagcagact gaccatcagc aaggacaaca gcaagagcca ggtgagcctg      240
aagctgagca gcgtgaccgc cgccgacacc gccgtgtact actgcgccag agagggctac     300
tactacggca ccacctacta cttcgactac tggggccagg gcaccaccgt gaccgtgagc     360
agc                                                                    363

<210> SEQ ID NO 55
<211> LENGTH: 121
<212> TYPE: PRT
<213> ORGANISM: Artificial Sequence
<220> FEATURE:
<223> OTHER INFORMATION: Synthesized

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Phe Glu Gly Ser Thr Asp Tyr Gln Ser Ala Leu Lys
    50                  55                  60

Ser Arg Val Thr Ile Ser Val Asp Thr Ser Lys Asn Gln Phe Ser Leu
```

-continued

```
                65              70              75              80

Lys Leu Ser Ser Val Thr Ala Ala Asp Thr Ala Val Tyr Tyr Cys Ala
                    85              90              95

Arg Glu Gly Tyr Tyr Tyr Gly Thr Thr Tyr Tyr Phe Asp Tyr Trp Gly
                100             105             110

Gln Gly Thr Thr Val Thr Val Ser Ser
        115             120
```

<210> SEQ ID NO 56
<211> LENGTH: 363
<212> TYPE: DNA
<213> ORGANISM: Artificial Sequence
<220> FEATURE:
<223> OTHER INFORMATION: Synthesized

<400> SEQUENCE: 56

```
caggtgcagc tgcaggagag cggccccggc ctggtgaagc ccagcgagac cctgagcctg       60
acctgcaccg tgagcggctt cagcctgacc ggctacggcg tgaactggat cagacagccc      120
cccggcaagg gcctggagtg gatcggcatg atctggttcg agggcagcac cgactaccag      180
agcgccctga gagcagagt gaccatcagc gtggacacca gcaagaacca gttcagcctg      240
aagctgagca gcgtgaccgc cgccgacacc gccgtgtact actgcgccag agagggctac      300
tactacggca ccacctacta cttcgactac tggggccagg gcaccaccgt gaccgtgagc      360
agc                                                                    363
```

<210> SEQ ID NO 57
<211> LENGTH: 121
<212> TYPE: PRT
<213> ORGANISM: Artificial Sequence
<220> FEATURE:
<223> OTHER INFORMATION: Synthesized

<400> SEQUENCE: 57

```
Gln Val Gln Leu Gln Glu Ser Gly Pro Gly Leu Val Lys Pro Ser Glu
1               5               10              15

Thr Leu Ser Leu Thr Cys Thr Val Ser Gly Phe Ser Leu Thr Gly Tyr
                20              25              30

Gly Val Asn Trp Ile Arg Gln Pro Pro Gly Lys Gly Leu Glu Trp Ile
            35              40              45

Gly Met Ile Trp Phe Glu Gly Ser Thr Asp Tyr Asn Ser Ala Leu Lys
        50              55              60

Ser Arg Val Thr Ile Ser Lys Asp Asn Ser Lys Ser Gln Val Ser Leu
65              70              75              80

Lys Leu Ser Ser Val Thr Ala Ala Asp Thr Ala Val Tyr Tyr Cys Ala
                    85              90              95

Arg Glu Gly Tyr Tyr Tyr Gly Thr Thr Tyr Tyr Phe Asp Tyr Trp Gly
                100             105             110

Gln Gly Thr Thr Val Thr Val Ser Ser
        115             120
```

<210> SEQ ID NO 58
<211> LENGTH: 363
<212> TYPE: DNA
<213> ORGANISM: Artificial Sequence
<220> FEATURE:
<223> OTHER INFORMATION: Synthesized

<400> SEQUENCE: 58

```
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gatcggcatg atctggttcg agggcagcac cgactacaac     180
agcgccctga gagcagagt gaccatcagc aaggacaaca gcaagagcca ggtgagcctg      240
aagctgagca gcgtgaccgc cgccgacacc gccgtgtact actgcgccag agagggctac     300
tactacggca ccacctacta cttcgactac tggggccagg gcaccaccgt gaccgtgagc     360
agc                                                                    363
```

<210> SEQ ID NO 59
<211> LENGTH: 121
<212> TYPE: PRT
<213> ORGANISM: Artificial Sequence
<220> FEATURE:
<223> OTHER INFORMATION: Synthesized

<400> SEQUENCE: 59

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Phe Asp Gly Ser Thr Asp Tyr Gln Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120
```

<210> SEQ ID NO 60
<211> LENGTH: 363
<212> TYPE: DNA
<213> ORGANISM: Artificial Sequence
<220> FEATURE:
<223> OTHER INFORMATION: Synthesized

<400> SEQUENCE: 60

```
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gatcggcatg atctggttcg acggcagcac cgactaccag     180
agcgccctga gagcagagt gaccatcagc aaggacaaca gcaagagcca ggtgagcctg      240
aagctgagca gcgtgaccgc cgccgacacc gccgtgtact actgcgccag agagggctac     300
tactacggca ccacctacta cttcgactac tggggccagg gcaccaccgt gaccgtgagc     360
agc                                                                    363
```

<210> SEQ ID NO 61
<211> LENGTH: 121
<212> TYPE: PRT
<213> ORGANISM: Artificial Sequence
<220> FEATURE:
<223> OTHER INFORMATION: Synthesized

<400> SEQUENCE: 61

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Phe Glu Gly Ser Thr Asp Tyr Gln Ser Ala Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120

<210> SEQ ID NO 62
<211> LENGTH: 363
<212> TYPE: DNA
<213> ORGANISM: Artificial Sequence
<220> FEATURE:
<223> OTHER INFORMATION: Synthesized

<400> SEQUENCE: 62
caggtgcagc tgcaggagag cggccccggc ctggtgaagc ccagcgagac cctgagcctg      60
acctgcaccg tgagcggctt cagcctgacc ggctacggcg tgaactggat cagacagccc     120
cccggcaagg gcctggagtg gatcggcatg atctggttcg agggcagcac cgactaccag     180
agcgccctga gagcagagt gaccatcagc aaggacaaca gcaagagcca ggtgagcctg     240
aagctgagca gcgtgaccgc cgccgacacc gccgtgtact actgcgccag agagggctac     300
tactacggca ccacctacta cttcgactac tggggccagg gcaccaccgt gaccgtgagc     360
agc                                                                     363

<210> SEQ ID NO 63
<211> LENGTH: 121
<212> TYPE: PRT
<213> ORGANISM: Artificial Sequence
<220> FEATURE:
<223> OTHER INFORMATION: Synthesized

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Leu
        35                  40                  45

Gly Met Ile Trp Phe Glu Gly Ser Thr Asp Tyr Gln Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

-continued

```
Arg Glu Gly Tyr Tyr Tyr Gly Thr Thr Tyr Tyr Phe Asp Tyr Trp Gly
            100                 105                 110

Gln Gly Thr Thr Val Thr Val Ser Ser
        115                 120

<210> SEQ ID NO 64
<211> LENGTH: 363
<212> TYPE: DNA
<213> ORGANISM: Artificial Sequence
<220> FEATURE:
<223> OTHER INFORMATION: Synthesized

<400> SEQUENCE: 64
caggtgcagc tgcaggagag cggccccggc ctggtgaagc ccagcgagac cctgagcctg        60
acctgcaccg tgagcggctt cagcctgacc ggctacggcg tgaactggat cagacagccc       120
cccggcaagg gcctggagtg gctgggcatg atctggttcg agggcagcac cgactaccag       180
agcgccctga agagcagact gaccatcagc aaggacaaca gcaagagcca ggtgagcctg       240
aagctgagca gcgtgaccgc cgccgacacc gccgtgtact actgcgccag agagggctac       300
tactacggca ccacctacta cttcgactac tggggccagg gcaccaccgt gaccgtgagc       360
agc                                                                     363
```